(12) United States Patent
Slusher et al.

(10) Patent No.: US 7,968,593 B2
(45) Date of Patent: Jun. 28, 2011

(54) THIOLACTONES

(75) Inventors: Barbara S. Slusher, Kingsville, MD (US); Takashi Tsukamoto, Ellicott City, MD (US)

(73) Assignee: Eisai Inc., Woodcliff Lake, NJ (US)

( * ) Notice: Subject to any disclaimer, the term of this patent is extended or adjusted under 35 U.S.C. 154(b) by 0 days.

(21) Appl. No.: 12/472,251

(22) Filed: May 26, 2009

(65) Prior Publication Data

US 2010/0048667 A1 Feb. 25, 2010

Related U.S. Application Data

(60) Continuation of application No. 11/830,737, filed on Jul. 30, 2007, now Pat. No. 7,553,866, which is a continuation of application No. 11/537,979, filed on Oct. 2, 2006, now abandoned, which is a division of application No. 10/791,278, filed on Mar. 3, 2004, now Pat. No. 7,125,907.

(51) Int. Cl.
*A61K 31/382* (2006.01)
*A61K 31/381* (2006.01)
*C07D 335/06* (2006.01)
*C07D 335/04* (2006.01)

(52) U.S. Cl. .......................................... 514/432; 549/23
(58) Field of Classification Search .................... 549/23; 514/432
See application file for complete search history.

(56) References Cited

U.S. PATENT DOCUMENTS

| | | | |
|---|---|---|---|
| 4,239,636 A | 12/1980 | Brois et al. |
| 5,672,592 A | 9/1997 | Jackson et al. |
| 5,795,877 A | 8/1998 | Jackson et al. |
| 5,804,602 A | 9/1998 | Slusher et al. |
| 5,824,662 A | 10/1998 | Slusher et al. |
| 5,863,536 A | 1/1999 | Jackson et al. |
| 5,880,112 A | 3/1999 | Jackson et al. |
| 5,902,817 A | 5/1999 | Jackson et al. |
| 5,962,521 A | 10/1999 | Jackson et al. |
| 5,968,915 A | 10/1999 | Jackson et al. |
| 5,977,090 A | 11/1999 | Slusher et al. |
| 5,981,209 A | 11/1999 | Slusher et al. |
| 5,985,855 A | 11/1999 | Slusher et al. |
| 6,004,946 A | 12/1999 | Slusher et al. |
| 6,011,021 A | 1/2000 | Slusher et al. |
| 6,017,903 A | 1/2000 | Slusher et al. |
| 6,025,344 A | 2/2000 | Jackson et al. |
| 6,025,345 A | 2/2000 | Jackson et al. |
| 6,028,216 A | 2/2000 | Morales et al. |
| 6,046,180 A | 4/2000 | Jackson et al. |
| 6,054,444 A | 4/2000 | Jackson et al. |
| 6,071,965 A | 6/2000 | Jackson et al. |
| 6,121,252 A | 9/2000 | Jackson et al. |
| 6,228,888 B1 | 5/2001 | Slusher |
| 6,265,609 B1 | 7/2001 | Jackson et al. |
| 6,271,245 B1 | 8/2001 | Jackson et al. |
| 6,288,046 B1 | 9/2001 | Jackson et al. |
| 6,313,159 B1 | 11/2001 | Jackson et al. |
| 6,348,464 B1 | 2/2002 | Jackson et al. |
| 6,372,726 B1 | 4/2002 | Slusher et al. |
| 6,376,478 B1 | 4/2002 | Slusher |
| 6,384,022 B1 | 5/2002 | Jackson et al. |
| 6,395,718 B1 | 5/2002 | Slusher et al. |
| 6,413,948 B1 | 7/2002 | Slusher et al. |
| 6,444,657 B1 | 9/2002 | Slusher et al. |
| 6,452,044 B2 | 9/2002 | Jackson et al. |
| 6,458,775 B1 | 10/2002 | Jackson et al. |
| 6,479,471 B1 | 11/2002 | Jackson et al. |
| 6,586,623 B2 | 7/2003 | Tsukamoto et al. |
| 6,740,777 B2 | 5/2004 | Tsukamoto et al. |
| 6,812,364 B2 | 11/2004 | Tsukamoto et al. |
| 7,125,907 B2 | 10/2006 | Slusher et al. |
| 7,553,866 B2 | 6/2009 | Slusher et al. |
| 2003/0017965 A1 | 1/2003 | Slusher et al. |
| 2003/0036534 A1 | 2/2003 | Slusher et al. |
| 2003/0064912 A1 | 4/2003 | Slusher et al. |
| 2003/0083374 A1 | 5/2003 | Jackson et al. |
| 2003/0083505 A1 | 5/2003 | Jackson et al. |
| 2003/0087897 A1 | 5/2003 | Tsukamoto et al. |
| 2003/0216468 A1 | 11/2003 | Tsukamoto et al. |
| 2004/0186081 A1 | 9/2004 | Slusher et al. |
| 2004/0198824 A1 | 10/2004 | Tsukamoto et al. |
| 2005/0004203 A1 | 1/2005 | Slusher et al. |
| 2007/0037798 A1 | 2/2007 | Slusher et al. |
| 2008/0004334 A1 | 1/2008 | Slusher et al. |

FOREIGN PATENT DOCUMENTS

| | | |
|---|---|---|
| CA | 2434117 A1 | 7/2002 |
| EP | 1 988 088 A1 | 11/2008 |
| FR | 2 819 253 | 7/2002 |
| WO | WO 94/05687 | 3/1994 |
| WO | WO 01/01974 A2 | 1/2001 |
| WO | WO 01/91738 A2 | 12/2001 |
| WO | WO 02/057222 B2 | 7/2002 |

OTHER PUBLICATIONS

Collins, *Expert Opin. Emerging Drugs* 10(1):95-108 (2005), in prior U.S. Appl. No. 10/791,278.
Direction to Request Examination mailed Jul. 31, 2007, herewith.
Derwent WPI Abstract (English language Abstract) for FR 2 819 253, in prior U.S. Appl. No. 10/791,278, Jul. 12, 2002.
Examiner's First Report, Australian Patent Application. No. 2004217969, herewith, (Jun. 11, 2009).
European Search Report, European Appln. No. 08 01 3761 (European Published Application No. EP 1 988 088 A1), (2008), in prior U.S. Appl. No. 11/830,737.
Hannessian et al., "N-Aryl Sulfonyl Homocysteine Hydroxamate Inhibitors of Matrix Metalloproteinases", *J. Med. Chem.* 44:3066-3073 (2001), in prior U.S. Appl. No. 10/791,278.
International Search Report (PCT/US2004/006178) (2004), in prior U.S. Appl. No. 10/791,278.

(Continued)

*Primary Examiner* — Jason M Nolan

(74) *Attorney, Agent, or Firm* — Myers Bigel Sibley & Sajovec, P.A.

(57) ABSTRACT

This invention provides new compounds, pharmaceutical compositions and diagnostic kits comprising such compounds, and methods of using such compounds for inhibiting NAALADase enzyme activity, detecting diseases where NAALADase levels are altered, inhibiting angiogenesis, effecting a TGF-β activity or a neuronal activity, and treating a glutamate abnormality, a compulsive disorder, neuropathy, pain, a prostate disease, cancer, Huntington's disease, diabetes, a retinal disorder or glaucoma.

13 Claims, 5 Drawing Sheets

OTHER PUBLICATIONS

Jackson et al., "Design of NAALADase Inhibitors: A Novel Neuroprotective Strategy", *Current Medicinal Chemistry* 8:949-957 (2001), in prior U.S. Appl. No. 10/791,278.

Morissette et al., "High-Throughout Crystallization: Polymorphs, Salts, Co-Crystals and Solvates of Pharmaceutical Solids", *Advanced Drug Delivery Reviews*, 56:275-300 (2004), in prior U.S. Appl. No. 11/537,979.

Non-Final Office Action, U.S. Appl. No. 11/537,979 (Oct. 2, 2006), herewith.

Non-Final Office Action, U.S. Appl. No, 11/830,737 (Jul. 30, 2007), herewith.

Takahata et al., "Regloselective Thio-Claisen Rearrangement", *Heterocycles* 24(12):3347-3350 (1986), in prior U.S. Appl. No. 10/791,278.

Tokmakov, "$\alpha$-Dimethylaminomethylene-$\gamma$-Thiobutyrolactone and Synthesis of Heterocyclic Derivatives", *Chemistry of Heterocycle Compounds* 32(2) (1996), in prior U.S. Appl. No. 10/791,278.

Written Opinion of the International Searching Authority—PCT Rule 43*bis*.1, mailed Jul. 30, 2004, herewith.

Ghadge et al., "Glutamate carboxypeptidase II inhibition protects motor neurons from death in familial amyotrophic lateral sclerosis models," *PNAS*, 100(16):9554-9559 (Aug. 5, 2003), herewith.

Jackson et al., "Design and Pharmacological Activity of Phosphinic Acid Based NAALADase Inhibitors," *J. Med. Chem*, 44:4170-4175 (2001), herewith.

Slusher et al., "Selective inhibition of NAALADase, which converts NAAG to glutamate, reduces ischemic brain injury," *Nature Medicine*, 3(12):1396-1402 (Dec. 1999), herewith.

THIOLACTONES

CROSS-REFERENCE TO RELATED APPLICATIONS

This application is a continuation of U.S. patent application Ser. No. 11/830,737, filed Jul. 30, 2007 now U.S. Pat. No. 7,553,866, which is a continuation of U.S. patent application Ser. No. 11/537,979, filed Oct. 2, 2006, (now abandoned) which is a divisional of U.S. patent application Ser. No. 10/791,278, filed Mar. 3, 2004, (now U.S. Pat. No. 7,125,907) which claims the benefit of U.S. Provisional Patent Application No. 60/450,648, filed Mar. 3, 2003, the entire contents of which applications are herein incorporated by reference.

This invention provides new compounds, pharmaceutical compositions and diagnostic kits comprising such compounds, and methods of using such compounds for inhibiting NAALADase enzyme activity, detecting diseases where NAALADase levels are altered, inhibiting angiogenesis, effecting a TGF-β activity or a neuronal activity, and treating a glutamate abnormality, a compulsive disorder, neuropathy, pain, a prostate disease, cancer, Huntington's disease, diabetes, a retinal disorder or glaucoma.

The NAALADase enzyme, also known as prostate specific membrane antigen ("PSMA") and human glutamate carboxypeptidase II ("GCP II"), catalyzes the hydrolysis of the neuropeptide N-acetyl-aspartyl-glutamate ("NAAG") to N-acetyl-aspartate ("NAA") and glutamate. Based upon amino acid sequence homology, NAALADase has been assigned to the M28 family of peptidases.

Studies suggest that inhibitors of NAALADase may be useful in treating ischemia, spinal cord injury, demyelinating diseases, Parkinson's disease, Amyotrophic Lateral Sclerosis ("ALS"), Huntington's disease, alcohol dependence, nicotine dependence, cocaine dependence, opioid dependence, cancer, neuropathy, pain and schizophrenia, and in inhibiting angiogenesis. In view of their potential therapeutic applications, a need exists for new NAALADase inhibitors and prodrugs thereof.

SUMMARY OF THE INVENTION

This invention provides a compound of formula I, II or III

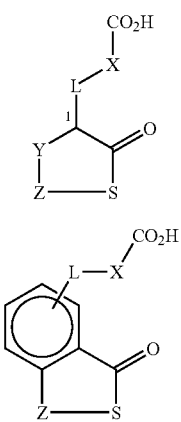

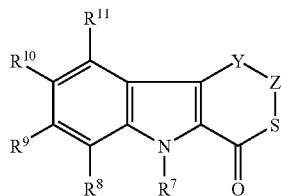

or a pharmaceutically acceptable equivalent, an optical isomer or a mixture of isomers of the compound, wherein:

X is $C_1$-$C_4$ alkylene, $C_2$-$C_4$ alkenylene, $C_2$-$C_4$ alkynylene, $C_3$-$C_8$ cycloalkylene, $C_5$-$C_7$ cycloalkenylene or Ar, wherein the alkylene, alkenylene, alkynylene, cycloalkylene or cycloalkenylene is unsubstituted or substituted with one or more substituent(s);

L is a bond, —$CR^1R^2$—, —O—, —S—, —$SO_2$— or —$NR^1$—;

Y is —O—, —S—, —$CR^3R^4$— or —$NR^3$—;

Z is —$(CR^5R^6)_n$—;

n is 1, 2, 3 or 4;

Ar is a bivalent aryl or heteroaryl radical that is unsubstituted or substituted with one or more substituent(s);

$R^1$, $R^2$, $R^3$, $R^4$, $R^5$ and $R^6$ are independently hydrogen, $C_1$-$C_4$ alkyl or $C_2$-$C_4$ alkenyl, wherein the alkyl or alkenyl is unsubstituted or substituted with one or more substituent(s);

$R^7$ is hydrogen, phenyl, phenylethyl or benzyl wherein the phenyl, phenylethyl or benzyl is unsubstituted or substituted with one or more substituent(s); and $R^8$, $R^9$, $R^{10}$ and $R^{11}$ are independently hydrogen, carboxy, hydroxy, halo, nitro, cyano, $C_1$-$C_4$ alkyl or $C_1$-$C_4$ alkoxy.

This invention further provides a pharmaceutical composition and a diagnostic kit comprising the compound, and a method of using the compound for inhibiting NAALADase enzyme activity, detecting a disease where NAALADase levels are altered, inhibiting angiogenesis, effecting a TGF-β activity or a neuronal activity, and treating a glutamate abnormality, a compulsive disorder, neuropathy, pain, a prostate disease, cancer, Huntington's disease, diabetes, a retinal disorder or glaucoma.

DETAILED DESCRIPTION

Definitions

Figure 1:
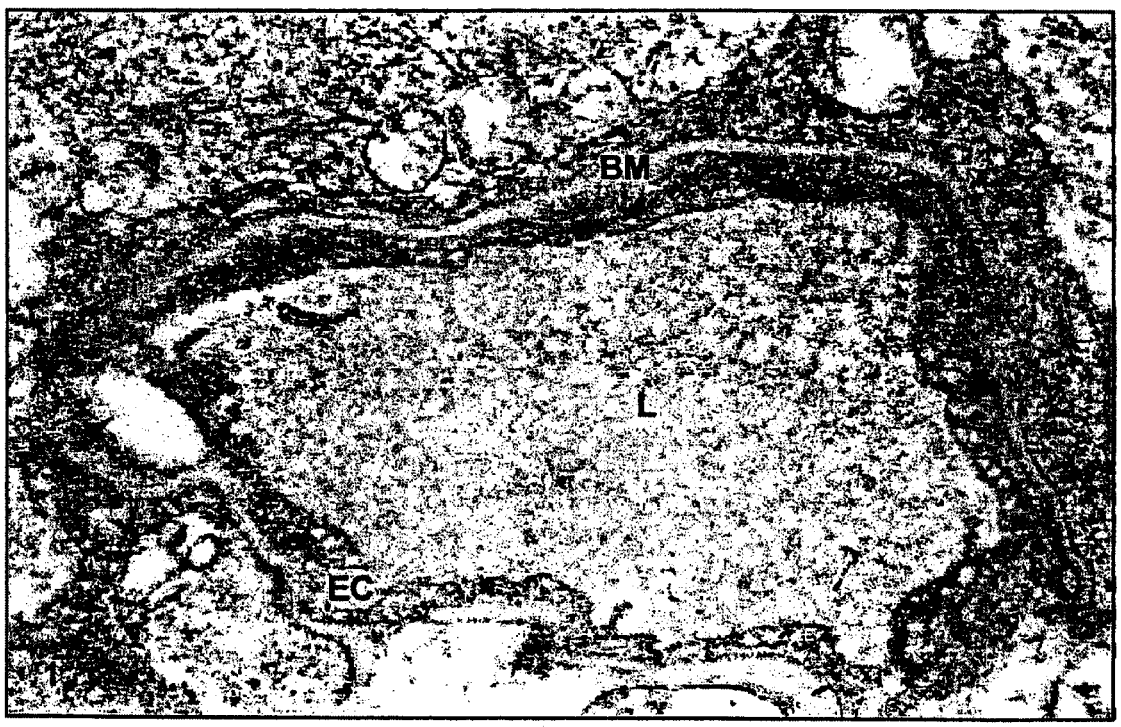
FIG. 1 is a 27,000× magnified photograph of a retinal blood vessel from a control, non-diabetic rat.

"Compound B" refers to 2-(3-sulfanylpropyl)pentanedioic acid.

"Compound D" refers to 2-(2-sulfanylethyl)pentanedioic acid.

"Compound E" refers to 3-carboxy-alpha-(3-mercaptopropyl)benzenepropanoic acid.

"Compound F" refers to 3-carboxy-5-(1,1-dimethylethyl)-alpha-(3-mercaptopropyl)benzenepropanoic acid.

"Alkyl" refers to a univalent, saturated straight or branched chain hydrocarbon radical. Examples include, without limitation, methyl, ethyl, propyl, iso-propyl, butyl, iso-butyl, tert-butyl, n-pentyl and n-hexyl.

"Alkylene" refers to a bivalent, saturated straight or branched chain hydrocarbon radical.

"Alkenyl" refers to a univalent, unsaturated straight or branched chain hydrocarbon radical comprising at least one carbon to carbon double bond. Examples include, without limitation, ethenyl, propenyl, iso-propenyl, butenyl, iso-butenyl, tert-butenyl, n-pentenyl and n-hexenyl.

"Alkenylene" refers to a bivalent, unsaturated straight or branched chain hydrocarbon radical comprising at least one carbon to carbon double bond.

"Alkynyl" refers to a univalent, unsaturated straight or branched chain hydrocarbon radical comprising at least one carbon to carbon triple bond. Examples include, without limitation, ethynyl, propynyl, iso-propynyl, butynyl, iso-butynyl, tert-butynyl, pentynyl and hexynyl.

"Alkynylene" refers to a bivalent, unsaturated straight or branched chain hydrocarbon radical comprising at least one carbon to carbon triple bond.

"Cycloalkyl" refers to a univalent, cyclic alkyl radical. Examples include, without limitation, cyclobutyl, cyclopentyl, cyclohexyl, cycloheptyl and cyclooctyl.

"Cycloalkylene" refers to a bivalent, cyclic alkyl radical.

"Cycloalkenyl" refers to a univalent, cyclic alkenyl radical. Examples include, without limitation, cyclopentenyl, cyclohexenyl, cycloheptenyl and cyclooctenyl.

"Cycloalkenylene" refers to a bivalent, cyclic alkenyl radical.

"Alkoxy" refers to an alkyl group bonded through an oxygen linkage.

"Alkenoxy" refers to an alkenyl group bonded through an oxygen linkage.

"Aryl" refers to a cyclic aromatic hydrocarbon moiety having one or more closed ring(s). Examples include, without limitation, phenyl, benzyl, naphthyl, anthracenyl, phenanthracenyl and biphenyl.

"Heteroaryl" refers to a cyclic aromatic moiety having one or more closed rings with one or more heteroatom(s) (for example, sulfur, nitrogen or oxygen) in at least one ring. Examples include, without limitation, pyrryl, furanyl, thienyl, pyridinyl, oxazolyl, thiazolyl, benzofuranyl, benzothienyl, benzofuranyl and benzothienyl.

"Carbocycle" refers to a hydrocarbon, cyclic moiety having one or more closed ring(s) that is/are alicyclic, aromatic, fused and/or bridged. Examples include, without limitation, cyclopropane, cyclobutane, cyclopentane, cyclohexane, cycloheptane, cyclopentene, cyclohexene, cycloheptene, cyclooctene, benzyl, naphthene, anthracene, phenanthracene, biphenyl and pyrene.

"Heterocycle" refers to a cyclic moiety having one or more closed rings that is/are alicyclic, aromatic, fused and/or bridged, with one or more heteroatoms (for example, sulfur, nitrogen or oxygen) in at least one of the rings. Examples include, without limitation, pyrrolidine, pyrrole, thiazole, thiophene, piperidine, pyridine, isoxazolidine and isoxazole.

"Halo" refers to a fluoro, chloro, bromo or iodo radical.

"Isosteres" refer to elements, functional groups, substituents, molecules or ions having different molecular formulae but exhibiting similar or identical physical properties. For example, tetrazole is an isostere of carboxylic acid because it mimics the properties of carboxylic acid even though they have different molecular formulae. Typically, two isosteric molecules have similar or identical volumes and shapes. Ideally, isosteric molecules should be isomorphic and able to co-crystallize. Other physical properties that isosteric molecules usually share include boiling point, density, viscosity and thermal conductivity. However, certain properties may be different: dipolar moments, polarity, polarization, size and shape since the external orbitals may be hybridized differently. The term "isosteres" encompasses "bioisosteres."

"Bioisosteres" are isosteres that, in addition to their physical similarities, share some common biological properties. Typically, bioisosteres interact with the same recognition site or produce broadly similar biological effects.

"Effective amount" refers to the amount required to produce a desired effect, for example, to inhibit NAALADase enzyme activity, to treat a glutamate abnormality, to effect a neuronal activity, to treat a prostate disease, to treat cancer, to inhibit angiogenesis, to effect a TGF-β activity, to treat Huntington's disease, to treat diabetes, to treat a retinal disorder or to treat glaucoma.

"Metabolite" refers to a substance produced by metabolism or by a metabolic process.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate. In addition, NAAG is an agonist at group II metabotropic glutamate receptors, specifically mGluR3 receptors; when attached to a moiety capable of inhibiting NAALADase, it is expected that metabotropic glutamate receptor ligands will provide potent and specific NAALADase inhibitors.

"NAALADase" refers to N-acetylated α-linked acidic dipeptidase, a membrane bound metallopeptidase which catabolizes NAAG to N-acetylaspartate ("NAA") and glutamate ("GLU"):

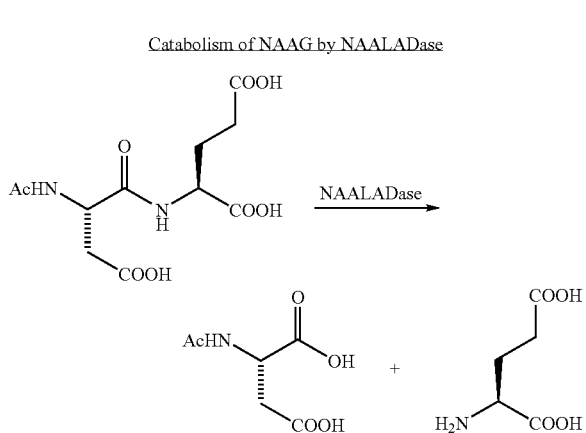

Catabolism of NAAG by NAALADase

NAALADase has been assigned to the M28 peptidase family and is also called PSMA or human GCP II, EC number 3.4.17.21. It is believed that NAALADase is a co-catalytic zinc/zinc metallopeptidase. NAALADase shows a high affinity for NAAG with a Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Inhibition," in the context of enzymes, refers to reversible enzyme inhibition such as competitive, uncompetitive and non-competitive inhibition. Competitive, uncompetitive and non-competitive inhibition can be distinguished by the effects of an inhibitor on the reaction kinetics of an enzyme. Competitive inhibition occurs when the inhibitor combines reversibly with the enzyme in such a way that it competes with a normal substrate for binding at the active site. The affinity between the inhibitor and the enzyme may be measured by the inhibitor constant, $K_i$, which is defined as:

$$K_i = \frac{[E][I]}{[EI]}$$

wherein [E] is the concentration of the enzyme, [I] is the concentration of the inhibitor, and [EI] is the concentration of the enzyme-inhibitor complex formed by the reaction of the enzyme with the inhibitor. Unless otherwise specified, $K_i$ refers to the affinity between the inventive compounds and NAALADase. Embodiments include a $K_i$ of less than 100 µM, less than 10 µM or less than 1 µM, as determined using any appropriate assay known in the art. "$IC_{50}$" is a related term used to define the concentration or amount of a compound that is required to cause a 50% inhibition of the target enzyme.

"Pharmaceutically acceptable carrier" refers to a pharmaceutically acceptable material, composition or vehicle, such as a liquid or solid filler, diluent, excipient or solvent encapsulating material, involved in carrying or transporting the subject compound from one organ, or portion of the body, to another organ or portion of the body. Each carrier is "acceptable" in the sense of being compatible with the other ingredients of the formulation and suitable for use with the patient. Examples of materials that can serve as a pharmaceutically acceptable carrier include, without limitation: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically acceptable equivalent" includes, without limitation, pharmaceutically acceptable salts, hydrates, solvates, metabolites, prodrugs and isosteres. Many pharmaceutically acceptable equivalents are expected to have the same or similar in vitro or in vivo activity as the compounds of the invention.

"Pharmaceutically acceptable salt" refers to an acid or base salt of the inventive compounds, which salt possesses the desired pharmacological activity and is neither biologically nor otherwise undesirable. The salt can be formed with acids that include, without limitation, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include, without limitation, ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

"Prodrug" refers to a derivative of the inventive compounds that undergoes biotransformation, such as metabolism, before exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using conventional methods, such as that described in BURGER'S MEDICINAL CHEMISTRY AND DRUG CHEMISTRY, Fifth Ed., Vol. 1, pp. 172-178, 949-982 (1995).

"Derivative" refers to a substance produced from another substance either directly or by modification or partial substitution.

"Radiosensitizer" refers to a low molecular weight compound administered to animals in therapeutically effective amounts to promote the treatment of diseases that are treatable with electromagnetic radiation. Diseases that are treatable with electromagnetic radiation include, without limitation, neoplastic diseases, benign and malignant tumors, and cancerous cells. Electromagnetic radiation treatment of other diseases not listed herein are also contemplated by this invention.

"Electromagnetic radiation" includes, without limitation, radiation having the wavelength of $10^{-20}$ to $10^0$ meters. Examples include, without limitation, gamma radiation ($10^{-20}$ to $10^{-13}$ m), X-ray radiation ($10^{-11}$ to $10^{-9}$ m), ultraviolet light (10 nm to 400 nm), visible light (400 nm to 700 nm), infrared radiation (700 nm to 1.0 mm) and microwave radiation (1 mm to 30 cm).

"Isomers" refer to compounds having the same number and kind of atoms, and hence the same molecular weight, but differing with respect to the arrangement or configuration of the atoms.

"Stereoisomers" refer to isomers that differ only in the arrangement of the atoms in space.

"Optical isomers" refer to enantiomers or diastereoisomers.

"Diastereoisomers" refer to stereoisomers that are not mirror images of each other. Diastereoisomers occur in compounds having two or more asymmetric carbon atoms; thus, such compounds have $2^n$ optical isomers, where n is the number of asymmetric carbon atoms.

"Enantiomers" refers to stereoisomers that are non-superimposable mirror images of one another.

"Enantiomer-enriched" refers to a mixture in which one enantiomer predominates.

"Racemic mixture" refers to a mixture containing equal parts of individual enantiomers.

"Non-racemic mixture" refers to a mixture containing unequal parts of individual enantiomers.

"Angiogenesis" refers to the process whereby new capillaries are formed. "Inhibition" of angiogenesis may be measured by many parameters and, for example, may be assessed by delayed appearance of neovascular structures, slowed development of neovascular structures, decreased occurrence of neovascular structures, slowed or decreased severity of angiogenesis-dependent disease effects, arrested angiogenic growth, or regression of previous angiogenic growth. In the extreme, complete inhibition is referred to herein as prevention. In relation to angiogenesis or angiogenic growth, "prevention" refers to no substantial angiogenesis or angiogenic growth if none has previously occurred, or no substantial additional angiogenesis or angiogenic growth if growth has previously occurred.

"Angiogenesis-dependent disease" includes, without limitation, rheumatoid arthritis, cardiovascular diseases, neovascular diseases of the eye, peripheral vascular disorders, dermatologic ulcers and cancerous tumor growth, invasion and metastasis.

"Animal" refers to a living organism having sensation and the power of voluntary movement, and which requires for its existence oxygen and organic food. Examples include, without limitation, members of the human, equine, porcine, bovine, murine, canine and feline species. In the case of a human, an "animal" may also be referred to as a "patient."

"Mammal" refers to a warm-blooded vertebrate animal.

"Anxiety" includes, without limitation, the emotional state consisting of psychophysiological responses to anticipation of unreal or imagined danger, ostensibly resulting from unrecognized intrapsychic conflict. Physiological concomitants include increased heart rate, altered respiration rate, sweating, trembling, weakness, and fatigue; psychological concomitants include feelings of impending danger, powerlessness, apprehension, and tension. *Dorland's Illustrated Medical Dictionary*, W.B. Saunders Co., 27th ed. (1988).

"Anxiety Disorder" includes, without limitation, mental disorders in which anxiety and avoidance behavior predominate. *Dorland's Illustrated Medical Dictionary*, W.B. Saunders Co., 27th ed. (1988). Examples include, without limitation, panic attack, agoraphobia, panic disorder, acute stress disorder, chronic stress disorder, specific phobia, simple phobia, social phobia, substance induced anxiety disorder, organic anxiety disorder, obsessive compulsive disorder, post-traumatic stress disorder, generalized anxiety disorder, and anxiety disorder NOS. Other anxiety disorders are characterized in *Diagnostic and Statistical Manual of Mental Disorders* (American Psychiatric Association 4th ed. 1994).

"Attention Deficit Disorder" ("ADD") refers to a disorder characterized by developmentally inappropriate inattention and impulsiveness, with or without hyperactivity. "Inattention" means a failure to finish tasks started, easily distracted, seeming lack of attention, and difficulty concentrating on tasks requiring sustained attention. "Impulsiveness" means acting before thinking, difficulty taking turns, problems organizing work, and constant shifting from one activity to another. "Hyperactivity" means difficulty staying seated and sitting still, and running or climbing excessively.

"Cancer" includes, without limitation, ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, prostate cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva, and Wilm's tumor.

"Compulsive disorder" refers to any disorder characterized by irresistible impulsive behavior. Examples of compulsive disorders include, without limitation, substance dependence, eating disorder, pathological gambling, ADD and Tourette's syndrome.

"Demyelinating disease" refers to any disease involving damage to or removal of the myelin sheath naturally surrounding nerve tissue, such as that defined in U.S. Pat. No. 5,859,046 and International Publication No. WO 98/03178, herein incorporated by reference. Examples include, without limitation, peripheral demyelinating diseases (such as Guillain-Barré syndrome, peripheral neuropathies and Charcot-Marie Tooth disease) and central demyelinating diseases (such as multiple sclerosis).

"Disease" refers to any deviation from or interruption of the normal structure or function of any part, organ or system (or combinations) of the body that is manifested by a characteristic set of symptoms and signs and whose etiology, pathology, and prognosis may be known or unknown. *Dorland's Illustrated Medical Dictionary*, (W.B. Saunders Co. 27th ed. 1988).

"Disorder" refers to any derangement or abnormality of function; a morbid physical or mental state. *Dorland's Illustrated Medical Dictionary*, (W.B. Saunders Co. 27th ed. 1988).

"Eating disorder" refers to compulsive overeating, obesity or severe obesity. Obesity means body weight of 20% over standard height-weight tables. Severe obesity means over 100% overweight.

"Glaucoma" includes, without limitation, chronic (idiopathic) open-angle glaucoma (e.g., high-pressure, normal-pressure); pupillary block glaucoma (e.g., acute angle-closure, subacute angle-closure, chronic angle-closure, combined-mechanism); developmental glaucoma (e.g., congenital (infantile), juvenile, Anxenfeld-Rieger syndrome, Peters' anomaly, Aniridia); glaucoma associated with other ocular disorders (e.g., glaucoma associated with disorder of the corneal endothelium, iris, ciliary body, lens, retina, choroid or vitreous); glaucoma associated with elevated episcleral venous pressure (e.g., systemic diseases with associated elevated intraocular pressure and glaucoma, corticosteroid-induced glaucoma); glaucoma associated with inflammation and trauma (e.g., glaucoma associated with keratitis, episcleritis, scleritis, uveitis, ocular trauma and hemorrhage); glaucoma following intraocular surgery (e.g., ciliary block (malignant) glaucoma, glaucoma in aphakia and pseudophakia, glaucoma associated with corneal surgery, glaucoma associated with vitreoretinal surgery).

"Glutamate abnormality" refers to any disease, disorder, or condition in which glutamate is implicated, including a pathological condition involving elevated levels of glutamate. Examples of a glutamate abnormality include, without limitation, compulsive disorder, spinal cord injury, epilepsy, stroke, ischemia, demyelinating disease, Alzheimer's disease, Parkinson's disease, ALS, Huntington's disease, schizophrenia, pain, peripheral neuropathy (including but not limited to diabetic neuropathy), traumatic brain injury, neuronal insult, inflammatory disease, anxiety, anxiety disorder, memory impairment, glaucoma and retinal disorder.

"Ischemia" refers to localized tissue anemia due to obstruction of the inflow of arterial blood. Global ischemia occurs when blood flow ceases for a period of time, as may result from cardiac arrest. Focal ischemia occurs when a portion of the body, such as the brain, is deprived of its normal blood supply, such as may result from thromboembolytic occlusion of a cerebral vessel, traumatic head injury, edema or brain tumor. Even if transient, both global and focal ischemia can produce widespread neuronal damage. Although nerve tissue damage occurs over hours or even days following the onset of ischemia, some permanent nerve tissue damage may develop in the initial minutes following cessation of blood flow to the brain. Much of this damage is attributed to glutamate toxicity and secondary consequences of reperfusion of the tissue, such as the release of vasoactive products by damaged endothelium, and the release of cytotoxic products, such as free radicals and leukotrienes, by the damaged tissue.

"Memory impairment" refers to a diminished mental registration, retention or recall of past experiences, knowledge, ideas, sensations, thoughts or impressions. Memory impairment may affect short and long-term information retention, facility with spatial relationships, memory (rehearsal) strategies, and verbal retrieval and production. Common causes of memory impairment are age, severe head trauma, brain anoxia or ischemia, alcoholic-nutritional diseases, drug intoxications and neurodegenerative diseases. For example, memory impairment is a common feature of neurodegenerative diseases such as Alzheimer's disease and senile dementia of the Alzheimer type. Memory impairment also occurs with other kinds of dementia, such as multi-infarct dementia, a senile dementia caused by cerebrovascular deficiency, and the Lewy-body variant of Alzheimer's disease with or without association with Parkinson's disease. Creutzfeldt-Jakob disease is a rare dementia with which memory impairment is associated. It is a spongiform encephalopathy caused by the prion protein; it may be transmitted from other sufferers or may arise from gene mutations. Loss of memory is also a common feature of brain-damaged patients. Brain damage may occur, for example, after a classical stroke or as a result of an anaesthetic accident, head trauma, hypoglycemia, carbon monoxide poisoning, lithium intoxication, vitamin ($B_1$, thiamine and $B_{12}$) deficiency, or excessive alcohol use. Korsakoff's amnesic psychosis is a rare disorder characterized by profound memory loss and confabulation, whereby the patient invents stories to conceal his or her memory loss. It is frequently associated with excessive alcohol intake. Memory impairment may furthermore be age-associated; the ability to recall information such as names, places and words seems to decrease with increasing age. Transient memory loss may also occur in patients, suffering from a major depressive disorder, after electro-convulsive therapy.

"Mental disorder" refers to any clinically significant behavioral or psychological syndrome characterized by the presence of distressing symptoms or significant impairment of functioning. Mental disorders are assumed to result from some psychological or organic dysfunction of the individual; the concept does not include disturbances that are essentially conflicts between the individual and society (social deviance).

"Metastasis" refers to "[t]he ability of cells of a cancer to disseminate and form new foci of growth at noncontiguous sites (i.e., to form metastases)." See Hill, R. P, "Metastasis", *The Basic Science of Oncology*, Tannock et al., Eds., McGraw-Hill, New York, pp. 178-195 (1992), herein incorporated by reference. "The transition from in situ tumor growth to metastatic disease is defined by the ability of tumor cells of the primary site to invade local tissues and to cross tissue barriers . . . . To initiate the metastatic process, carcinoma cells must first penetrate the epithelial basement membrane and then invade the interstitial stroma. For distant metastases, intravasation requires tumor cell invasion of the subendothelial basement membrane that must also be negotiated during tumor cell extravasation . . . . The development of malignancy is also associated with tumor-induced angiogenesis [which] not only allows for expansion of the primary tumors, but also permits easy access to the vascular compartment due to defects in the basement membranes of newly formed vessels." See Aznavoorian et al., *Cancer* (1993) 71:1368-1383, herein incorporated by reference.

"Neuropathy" refers to any disease or malfunction of the nerves. Neuropathy includes, without limitation, peripheral neuropathy, diabetic neuropathy, autonomic neuropathy and mononeuropathy. Peripheral neuropathy may be idiopathic or induced by any causes including diseases (for example, amyloidosis, alcoholism, HIV, syphilis, virus, autoimmune disorder, cancer, porphyria, arachnoiditis, post herpetic neuralgia, Guillain-Barré syndrome, diabetes including type I and type II diabetes), chemicals (for example, toxins, lead, dapsone, vitamins, paclitaxel chemotherapy, HAART therapy) and physical injuries to a particular nerve or nerve plexus (for example, trauma, compression, constriction).

"Neuroprotective" refers to the effect of reducing, arresting or ameliorating nervous insult, and protecting, resuscitating or reviving nervous tissue that has suffered nervous insult.

"Nervous insult" refers to any damage to nervous tissue and any disability or death resulting therefrom. The cause of nervous insult may be metabolic, toxic, neurotoxic, iatrogenic, thermal or chemical, and includes, without limitation, ischemia, hypoxia, cerebrovascular accident, trauma, surgery, pressure, mass effect, hemorrhage, radiation, vasospasm, neurodegenerative disease, neurodegenerative process, infection, Parkinson's disease, ALS, myelination/demyelination processes, epilepsy, cognitive disorder, glutamate abnormality and secondary effects thereof.

"Nervous tissue" refers to the various components that make up the nervous system, including without limitation neurons, neural support cells, glia, Schwann cells, vasculature contained within and supplying these structures, the central nervous system, the brain, the brain stem, the spinal cord, the junction of the central nervous system with the peripheral nervous system, the peripheral nervous system and allied structures.

"Pain" refers to localized sensations of discomfort, distress or agony, resulting from the stimulation of specialized nerve endings. It serves as a protective mechanism insofar as it induces the sufferer to remove or withdraw from the source. *Dorland's Illustrated Medical Dictionary*, (W.B. Saunders Co. 27th ed. 1988). Examples of pain include, without limitation, acute, chronic, cancer, burn, incisional, inflammatory, neuropathic and back pain.

"Neuropathic pain" refers to a condition of pain associated with a nerve injury. Depending on the particular syndrome, the pain may be due to alterations of the brain or spinal cord or may be due to abnormalities in the nerve itself. Neuropathic pain may be idiopathic or induced by any causes including diseases (for example, amyloidosis, alcoholism, HIV, syphilis, virus, autoimmune disorder, cancer, porphyria, arachnoiditis, post herpetic neuralgia, Guillain-Barré syndrome, diabetes including type I and type II diabetes), chemicals (for example, toxins, lead, dapsone, vitamins, paclitaxel chemotherapy, HAART therapy) and physical injuries to a particular nerve or nerve plexus (for example, trauma, compression, constriction).

"Pathological gambling" refers to a condition characterized by a preoccupation with gambling. Similar to psychoactive substance abuse, its effects include development of tolerance with a need to gamble progressively larger amounts of money, withdrawal symptoms, and continued gambling despite severe negative effects on family and occupation.

"Prostate disease" refers to any disease affecting the prostate. Examples of prostate disease include, without limitation, prostate cancer (e.g., adenocarcinoma and metastatic cancers of the prostate) and conditions characterized by abnormal growth of prostatic epithelial cells (e.g., benign prostatic hyperplasia).

"Retinal disorder" refers to vascular retinopathy, for example, hypertensive retinopathy, diabetic retinopathy (nonproliferative or proliferative), central retinal artery occlusion, or central retinal vein occlusion; age-related macular degeneration; retinal detachment; or retinitis pigmentosa.

"Schizophrenia" refers to a mental disorder or group of mental disorders characterized by disturbances in form and content of thought (loosening of associations, delusions, hallucinations), mood (blunted, flattened, inappropriate affect), sense of self and relationship to the external world (loss of ego boundaries, dereistic thinking, and autistic withdrawal), and behavior (bizarre, apparently purposeless, and stereotyped activity or inactivity). Examples of schizophrenia include, without limitation, acute, ambulatory, borderline, catatonic, childhood, disorganized, hebephrenic, latent, nuclear, paranoid, paraphrenic, prepsychotic, process, pseudoneurotic, pseudopsychopathic, reactive, residual, schizo-affective and undifferentiated schizophrenia. *Dorland's Illustrated Medical Dictionary* (W.B. Saunders Co. 27th ed. 1988).

"TGF-β" refers to transforming growth factor beta. TGF-β is recognized as a prototype of multifunctional growth factors. It regulates various cell and tissue functions, including cell growth and differentiation, angiogenesis, wound healing, immune function, extracellular matrix production, cell chemotaxis, apoptosis and hematopoiesis.

"TGF-β abnormality" refers to any disease, disorder or condition in which TGF-P is implicated, including diseases disorders and conditions characterized by an abnormal level of TGF-β.

"Abnormal level of TGF-β" refers to a measurable variance from normal levels of TGF-β, as determined by one of ordinary skill in the art using known techniques.

"Therapeutic window of opportunity" or "window" refers, in relation to stroke, to the maximal delay between the onset of stroke and the initiation of efficacious therapy.

"Tourette's syndrome" refers to an autosomal multiple tic disorder characterized by compulsive swearing, multiple muscle tics and loud noises. Tics are brief, rapid, involuntary movements that can be simple or complex; they are stereotyped and repetitive, but not rhythmic. Simple tics, such as eye blinking, often begin as nervous mannerisms. Complex tics often resemble fragments of normal behavior.

Unless otherwise defined in conjunction with a specific disease, disorder or condition, "treating" refers to:

(i) preventing a disease, disorder or condition from occurring in an animal that may be predisposed to the disease, disorder and/or condition but has not yet been diagnosed as having it;

(ii) inhibiting the disease, disorder or condition, i.e., arresting its development; and/or (iii) relieving the disease, disorder or condition, i.e., causing regression of the disease, disorder and/or condition.

"Treating ALS" refers to:

(i) preventing ALS from occurring in an animal that may be predisposed to ALS but has not yet been diagnosed as having it;

(ii) inhibiting ALS, e.g. arresting its development;

(iii) relieving ALS, e.g. causing regression of the disease, disorder and/or condition;

(iv) delaying onset of ALS or ALS symptom(s);

(v) slowing progression of ALS or ALS symptom(s);

(vi) prolonging survival of an animal suffering from ALS; and/or (vii) attenuating ALS symptom(s).

"Treating Huntington's disease" refers to:

(i) preventing Huntington's disease from occurring in an animal that may be predisposed to Huntington's disease but has not yet been diagnosed as having it;

(ii) inhibiting or slowing Huntington's disease, e.g. arresting its development;

(iii) relieving Huntington's disease, e.g. causing its regression;

(iv) improving motor coordination in an animal having Huntington's disease; and/or (v) prolonging survival of an animal having Huntington's disease.

"Treating substance dependence" refers to preventing relapse; reducing craving; suppressing tolerance; preventing, inhibiting and/or relieving withdrawal; attenuating sensitization; preventing, inhibiting (i.e. arresting development of) and/or relieving (i.e. causing regression of) substance-induced neurotoxicity; and/or preventing, inhibiting and/or relieving fetal alcohol syndrome.

"Craving" refers to a strong desire for a substance and/or a compelling urge and/or an irresistible impulse to use a substance.

"Dependence" refers to a maladaptive pattern of substance use, leading to clinically significant impairment or distress. Dependence is typically characterized by tolerance and/or withdrawal. Substances for which dependence may be developed include, without limitation, depressants (opioids, synthetic narcotics, barbiturates, glutethimide, methyprylon, ethchlorvynol, methaqualone, alcohol); anxiolytics (diazepam, chlordiazepoxide, alprazolam, oxazepam, temazepam); stimulants (amphetamine, methamphetamine, cocaine, nicotine); and hallucinogens (LSD, mescaline, peyote, marijuana).

"Opioid" refers to a narcotic analgesic that is either semi or fully synthetic, including, but not limited to Codeine, Morphine, Heroin, Hydromorphone (Dilaudid), Oxycodone (Percodan), Oxymorphone (Numorphan), Hydrocodone (Vicodin), Meperidine (Demerol), Fentanyl, Methadone (Dolophine), Darvon, Talwin.

"Relapse" refers to a return to substance use after a period of abstinence, often accompanied by reinstatement.

"Reinstatement" refers to a return to a preexisting level of use and dependence in a person who has resumed substance use following a period of abstinence.

"Sensitization" refers to a condition in which the response to a substance increases with repeated use.

"Tolerance" refers to an acquired reaction to a substance characterized by diminished effect with continued use of the same dose and/or a need for increased doses to achieve intoxication or desired effect previously achieved by lower doses. Both physiological and psychosocial factors may contribute to the development of tolerance. With respect to physiological tolerance, metabolic and/or functional tolerance may develop. By increasing the rate of metabolism of the substance, the body may be able to eliminate the substance more readily. Functional tolerance is defined as a decrease in sensitivity of the central nervous system to the substance. "Opioid tolerance" includes without limitation the failure of a steady dose of the drug to sustain the desired pharmacological effect over time, i.e., the need to increase the drug dosage to maintain the original pharmacological effect.

"Withdrawal" refers to a syndrome characterized by untoward physical changes that occur following cessation of or reduction in substance use, or administration of a pharmacologic antagonist.

One of ordinary skill in the art will recognize that there are alternative nomenclatures, nosologies and classification systems for the diseases, disorders and conditions defined above, and that such systems evolve with medical scientific progress.

Unless the context clearly dictates otherwise, the definitions of singular terms may be extrapolated to apply to their plural counterparts as they appear in the application; likewise, the definitions of plural terms may be extrapolated to apply to their singular counterparts as they appear in the application.

Compounds

This invention provides a compound of formula I, II or III or a pharmaceutically acceptable equivalent, an optical isomer or a mixture of isomers of the compound, wherein:

X is $C_1$-$C_4$ alkylene, $C_2$-$C_4$ alkenylene, $C_2$-$C_4$ alkynylene, $C_3$-$C_8$ cycloalkylene, $C_5$-$C_7$ cycloalkenylene or Ar, wherein the alkylene, alkenylene, alkynylene, cycloalkylene or cycloalkenylene is unsubstituted or substituted with one or more substituent(s);

L is a bond, —$CR^1R^2$—, —O—, —S—, —$SO_2$— or —$NR^1$—;

Y is —O—, —S—, —$CR^3R^4$— or —$NR^3$—;

Z is —$(CR^5R^6)_n$—;

n is 1, 2, 3 or 4;

Ar is a bivalent aryl or heteroaryl radical that is unsubstituted or substituted with one or more substituent(s);

$R^1$, $R^2$, $R^3$, $R^4$, $R^5$ and $R^6$ are independently hydrogen, $C_1$-$C_4$ alkyl or $C_2$-$C_4$ alkenyl, wherein the alkyl or alkenyl is unsubstituted or substituted with one or more substituent(s);

$R^7$ is hydrogen, phenyl, phenylethyl or benzyl wherein the phenyl, phenylethyl or benzyl is unsubstituted or substituted with one or more substituent(s); and $R^8$, $R^9$, $R^{10}$ and $R^{11}$ are independently hydrogen, carboxy, hydroxy, halo, nitro, cyano, $C_1$-$C_4$ alkyl or $C_1$-$C_4$ alkoxy.

In one embodiment of the compound of formula I, when L is a bond and X is ethyl, then Y is not —$CR^3R^4$—.

In another embodiment of the compound of formula I:
Y is —$CR^3R^4$—; and
n is 1 or 2.

In a further embodiment of the compound of formula I:
L is —$CR^1R^2$—, —O—, —S— or NH;
X is $C_1$-$C_2$ alkylene or Ar; and
Ar is phenylene, biphenylene, benzylene or naphthylene, wherein the phenylene, biphenylene, benzylene or naphthylene is unsubstituted or substituted with one or more substituent(s) independently selected from carboxy, halo, nitro, $C_1$-$C_4$ alkyl, $C_1$-$C_4$ alkoxy, phenyl, phenoxy and benzyloxy.

In one embodiment of the compound of formula II:
L is a bond, —$CR^1R^2$— or —O—; and
n is 2.

In another embodiment of the compound of formula II:
X is $C_1$-$C_4$ alkylene or Ar; and
Ar is phenylene, biphenylene or benzylene that is unsubstituted or substituted with one or more substituent(s) independently selected from carboxy, halo, nitro, $C_1$-$C_4$ alkyl, $C_1$-$C_4$ alkoxy, phenoxy and benzyloxy.

In one embodiment of the compound of formula III:
$R^8$, $R^9$, $R^{10}$ and $R^{11}$ are independently hydrogen or carboxy.

In another embodiment of the compound of formula III:
$R^7$ is phenyl or benzyl substituted with one or more substituent(s) independently selected from carboxy, halo, $C_1$-$C_4$ alkyl and $C_1$-$C_4$ alkoxy.

Examples of the one or more substituent(s) by which X, Ar, $R^1$, $R^2$, $R^3$, $R^4$, $R^5$, $R^6$ and $R^7$ may be substituted include, without limitation: $C_1$-$C_4$ alkyl, $C_2$-$C_4$ alkenyl, $C_2$-$C_4$ alkynyl, $C_1$-$C_4$ alkoxy, $C_2$-$C_4$ alkenyloxy, phenoxy, benzyloxy, hydroxy, carboxy, hydroperoxy, carbamido, carbamoyl, carbamyl, carbonyl, carbozoyl, amino, hydroxyamino, formamido, formyl, guanyl, cyano, cyanoamino, isocyano, isocyanato, diazo, azido, hydrazino, triazano, nitrilo, nitro, nitroso, isonitroso, nitrosamino, imino, nitrosimino, oxo, $C_1$-$C_4$ alkylthio, sulfamino, sulfamoyl, sulfeno, sulfhydryl, sulfinyl, sulfo, sulfonyl, thiocarboxy, thiocyano, isothiocyano, thioformamido, halo, haloalkyl, chlorosyl, chloryl, perchloryl, trifluoromethyl, iodosyl, iodyl, phosphino, phosphinyl, phospho, phosphono, arsino, selanyl, disilanyl, siloxy, silyl, silylene and carbocyclic and heterocyclic moieties.

The definition of any variable substituent at a particular location in a molecule is independent of its definitions elsewhere in that molecule. Substituents and substitution patterns on the inventive compounds can be selected by one of ordinary skill in the art to provide compounds that are chemically stable and that can be readily synthesized by techniques known in the art as well as those methods set forth herein.

Since the inventive compounds may possess one or more asymmetric carbon center(s), they may be capable of existing in the form of optical isomers as well as in the form of racemic or non-racemic mixtures of optical isomers. The optical isomers can be obtained by resolution of the racemic mixtures according to conventional processes. One such process entails formation of diastereoisomeric salts by treatment with an optically active acid or base, then separation of the mixture of diastereoisomers by crystallization, followed by liberation of the optically active bases from the salts. Examples of appropriate acids are tartaric, diacetyltartaric, dibenzoyltartaric, ditoluoyltartaric and camphorsulfonic acid.

A different process for separating optical isomers involves the use of a chiral chromatography column optimally chosen to maximize the separation of the enantiomers. Still another available process involves synthesis of covalent diastereoisomeric molecules, for example, esters, amides, acetals and ketals, by reacting the inventive compounds with an optically active acid in an activated form, an optically active diol or an optically active isocyanate. The synthesized diastereoisomers can be separated by conventional means such as chromatography, distillation, crystallization or sublimation, and then hydrolyzed to deliver the enantiomerically pure compound. In some cases hydrolysis to the "parent" optically active drug is not necessary prior to dosing the patient, since the compound can behave as a prodrug. The optically active compounds of this invention likewise can be obtained by utilizing optically active starting materials.

The compounds of this invention encompass individual optical isomers as well as racemic and non-racemic mixtures. In some non-racemic mixtures, the R configuration may be enriched while in other non-racemic mixtures, the S configuration may be enriched.

Examples of the inventive compounds include, without limitation, the compounds set forth in TABLE I.

TABLE I

REPRESENTATIVE COMPOUNDS

| Compound Number | Structure | Name |
|---|---|---|
| 1 | 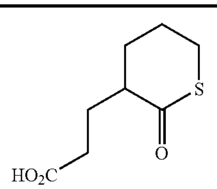 | 3-(2-Oxo-tetrahydro-thiopyran-3-yl)-propionic acid |
| 2 | 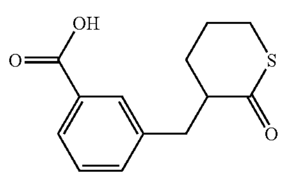 | 3-[(2-oxotetrahydro-2H-thiopyran-3-yl)methyl]benzoic acid |
| 3 | 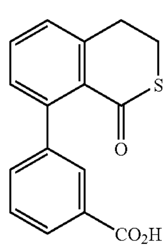 | 3-(1-Oxo-isothiochroman-8-yl)-benzoic acid |
| 4 | | 3-(1-Oxo-isothiochroman-8-yloxymethyl)-benzoic acid |
| 5 | | 3-(1-Oxo-3,4-dihydro-1H-2-thia-9-aza-fluoren-9-yl)-benzoic acid |

Methods of Use

While the inventive compounds are generally prodrugs of NAALADase inhibitors, the inventive compounds may also exhibit NAALADase inhibiting activity on their own. Whether by inhibiting NAALADase activity, by converting in vivo into compounds that inhibit NAALADase activity, or by another mechanism of action, the inventive compounds may be useful in the following therapeutic applications.

Method for Inhibiting NAALADase Enzyme Activity

This invention further provides a method for inhibiting NAALADase enzyme activity in an animal or a mammal, comprising administering to the animal or mammal an effective amount of a compound of formula I, II or III, as defined above.

Method for Treating Glutamate Abnormalities

Without being bound to any particular mechanism of action, the inventive compounds may block glutamate release pre-synaptically without interacting with post-synaptic glutamate receptors. Such compounds would be devoid of the behavioral toxicities associated with post-synaptic glutamate antagonists. Thus, this invention further provides a method for treating a glutamate abnormality in an animal or a mammal, comprising administering to the animal or mammal an effective amount of a compound of formula I, II or III, as defined above.

The glutamate abnormality that is treated by the inventive method may be selected from compulsive disorder, stroke, ischemia, demyelinating disease, Parkinson's disease, ALS, Huntington's disease, schizophrenia, diabetic neuropathy, pain, anxiety, anxiety disorder, memory impairment and glaucoma. In one embodiment, the inventive method is for treating a compulsive disorder selected from alcohol, nicotine, cocaine and opioid dependence. In another embodiment, the inventive method is for treating opioid tolerance.

Stroke patients often experience a significant temporal delay between the onset of ischemia and the initiation of therapy. Thus, there is a need for neuroprotectants with a long therapeutic window of opportunity. It is expected that the inventive compounds have a therapeutic window of opportunity of at least 1 hour. Accordingly, when the glutamate abnormality is stroke, the compound of the invention may be administered to the animal or mammal for up to 60 minutes, 120 minutes or more following onset of stroke.

Method for Effecting Neuronal Activities

This invention further provides a method for effecting a neuronal activity in an animal or a mammal, comprising administering to the animal or mammal an effective amount of a compound of formula I, II or III, as defined above.

The neuronal activity that is effected by the inventive method may be stimulation of damaged neurons, promotion of neuronal regeneration, prevention of neurodegeneration or treatment of a neurological disorder.

Examples of a neurological disorder that is treated by the inventive method include, without limitation: trigeminal neuralgia; glossopharyngeal neuralgia; Bell's Palsy; myasthenia gravis; muscular dystrophy; ALS; progressive muscular atrophy; progressive bulbar inherited muscular atrophy; herniated, ruptured or prolapsed invertebrate disk syndromes; cervical spondylosis; plexus disorders; thoracic outlet destruction syndromes; neuropathy; pain; Alzheimer's disease; Parkinson's disease; ALS; and Huntington's disease.

In one embodiment, the inventive method is for treating a neurological disorder selected from neuropathy (for example, peripheral neuropathy or diabetic neuropathy), pain (for example, neuropathic pain such as neuropathic pain induced by diabetes), traumatic brain injury, physical damage to spinal cord, stroke associated with brain damage, demyelinating disease and neurological disorder relating to neurodegeneration.

When the neurological disorder is pain, the compound of the invention may be administered in combination with an effective amount of morphine.

Examples of a neurological disorder relating to neurodegeneration include, without limitation, Alzheimer's disease, Parkinson's disease and ALS.

Method for Treating Prostate Diseases

This invention further provides a method for treating a prostate disease in an animal or a mammal, comprising administering to the animal or mammal an effective amount of a compound of formula I, II or III, as defined above. In one embodiment, the prostate disease is prostate cancer.

Method for Treating Cancers

This invention further provides a method for treating cancer in an animal or a mammal, comprising administering to the animal or mammal an effective amount of a compound of formula I, II or III, as defined above. In one embodiment, the cancer is in tissues where NAALADase resides, such as the brain, kidney and testis.

Method for Inhibiting Angiogenesis

This invention further provides a method for inhibiting angiogenesis in an animal or a mammal, comprising administering to the animal or mammal an effective amount of a compound of formula I, II or III, as defined above.

Angiogenesis may be necessary for fertility or metastasis of cancer tumors, or may be related to an angiogenic-dependent disease. Thus, this invention further provides a method for treating an angiogenic-dependent disease. Examples of an angiogenic-dependent disease include, without limitation, rheumatoid arthritis, cardiovascular diseases, neovascular diseases of the eye, peripheral vascular disorders, dermatologic ulcers and cancerous tumor growth, invasion or metastasis.

Method for Effecting TGF-β Activity

This invention further provides a method for effecting a TGF-β activity in an animal or a mammal, comprising administering to the animal or mammal an effective amount of a compound of formula I, II or III, as defined above.

The effecting a TGF-β activity includes increasing, reducing or regulating TGF-β levels, and treating a TGF-β abnormality. Examples of a TGF-β abnormality that is treated by the inventive method include neurodegenerative disorders, extra-cellular matrix formation disorders, cell-growth related diseases, infectious diseases, immune related diseases, epithelial tissue scarring, collagen vascular diseases, fibroproliferative disorders, connective tissue disorders, inflammation, inflammatory diseases, respiratory distress syndrome, infertility and diabetes.

Examples of a neurodegenerative disorder include, without limitation, neural tissue damage resulting from ischemia, reperfusion injury, myelination or neurodegeneration.

Examples of a cell-growth related disorder include, without limitation, disorders affecting kidney cells, hematopoietic cells, lymphocytes, epithelial cells or endothelial cells.

Examples of an infectious disease include, without limitation, diseases caused by a macrophage pathogen, particularly a macrophage pathogen selected from bacteria, yeast, fungi, viruses, protozoa, *Trypanosoma cruzi*, *Histoplasma capsulatum*, *Candida albicans*, *Candida parapsilosis*, *Cryptococcus neoformans*, *Salmonella*, *Pneumocystis*, *Toxoplasma*, *Listeria*, *Mycobacteria*, *Rickettsia* and *Leishmania*. Examples of *Mycobacteria* include, without limitation, *Mycobacterium tuberculosis* and *Mycobacterium leprae*. Examples of *Toxoplasma* include, without limitation, *Toxoplasma gondii*. Examples of *Rickettsia* include, without limitation, *R. prowazekii*, *R. coronii* and *R. tsutsugamushi*. Other examples of an infectious disease include single or multiple cutaneous lesions, mucosal disease, Chagas' disease, acquired immunodeficiency syndrome (AIDS), toxoplasmosis, leishmaniasis, trypanosomiasis, shistosomiasis, cryptosporidiosis, *Mycobacterium avium* infections, *Pneumocystis carinii* pneumonia and leprosy.

Examples of an immune related disease include, without limitation, autoimmune disorders; impaired immune function; and immunosuppression associated with an infectious disease, particularly, trypanosomal infection, viral infection, human immunosuppression virus, human T cell lymphotropic virus (HTLV-1), lymphocytic choriomeningitis virus or hepatitis.

Examples of a collagen vascular disease include, without limitation, progressive systemic sclerosis ("PSS"), polymyositis, scleroderma, dermatomyositis, eosinophilic fascitis, morphea, Raynaud's syndrome, interstitial pulmonary fibrosis, scleroderma and systemic lupus erythematosus.

Examples of a fibroproliferative disorder include, without limitation, diabetic nephropathy, kidney disease, proliferative vitreoretinopathy, liver cirrhosis, biliary fibrosis and myelofibrosis. Examples of a kidney disease include, without limitation, mesangial proliferative glomerulonephritis, crescentic glomerulonephritis, diabetic neuropathy, renal interstitial fibrosis, renal fibrosis in transplant patients receiving cyclosporin, and HIV-associated nephropathy.

Examples of a connective tissue disorder include, without limitation, scleroderma, myelofibrosis, and hepatic, intraocular and pulmonary fibrosis.

Without being limited to any particular mechanism of action, the inventive compounds may treat inflammatory diseases by regulating TGF-β and/or inhibiting myeloperoxidase. Examples of an inflammatory disease that is treated by the inventive method include, without limitation, a disease associated with PSS, polymyositis, scleroderma, dermatomyositis, eosinophilic fascitis, morphea, Raynaud's syndrome, interstitial pulmonary fibrosis, scleroderma, systemic lupus erythematosus, diabetic nephropathy, kidney disease, proliferative vitreoretinopathy, liver cirrhosis, biliary fibrosis, myelofibrosis, mesangial proliferative glomerulonephritis, crescentic glomerulonephritis, diabetic neuropathy, renal interstitial fibrosis, renal fibrosis in transplant patients receiving cyclosporin, and HIV-associated nephropathy.

Other uses associated with the inventive compounds' TGF-β regulating properties include:

stimulating growth of tissues, glands or organs, particularly growth that would enhance milk production or weight gain;

stimulating cell proliferation, particularly proliferation of fibroblasts, mesenchymal cells or epithelial cells;

inhibiting cell growth, particularly of epithelial cells, endothelial cells, T and B lymphocytes or thymocytes;

inhibiting expression of adipose, skeletal muscle or hematopoietic phenotypes, neoplasms, non-cytocidal viral or other pathogenic infections or autoimmune disorders;

mediating disease resistance or susceptibility;

suppressing cellular immune response;

inhibiting scar tissue formation, such as in skin or other epithelial tissue that has been damaged by wounds resulting from accidental injury, surgical operations, trauma-induced lacerations or other trauma, or by wounds involving the peritoneum for which the excessive connective tissue formation is abdominal adhesions;

increasing the effectiveness of a vaccine, particularly a vaccine for an allergy towards, for example, dust or hayfever; and inhibiting polyp formation.

Administration and Dosage

The inventive compounds may be administered by any means known to one of ordinary skill in the art. For example, the inventive compounds may be administered orally, parenterally, by inhalation spray, topically, rectally, nasally, buccally, vaginally, or via an implanted reservoir. The term "parenteral" as used herein includes subcutaneous, intravenous, intramuscular, intraperitoneal, intrathecal, intraventricular, intrasternal, intracranial, and intraosseous injection and infusion techniques. The exact administration protocol will vary depending upon various factors including the age, body weight, general health, sex and diet of the patient; the determination of specific administration procedures would be routine to an one of ordinary skill in the art.

The inventive compounds may be administered by a single dose, multiple discrete doses or continuous infusion. Pump means, particularly subcutaneous pump means, are useful for continuous infusion.

Dose levels on the order of about 0.001 mg/kg/d to about 10,000 mg/kg/d of an inventive compound are useful for the inventive methods. In one embodiment, the dose level is about 0.1 mg/kg/d to about 1,000 mg/kg/d. In another embodiment, the dose level is about 1 mg/kg/d to about 100 mg/kg/d. The specific dose level for any particular patient will vary depending upon various factors, including the activity and the possible toxicity of the specific compound employed; the age, body weight, general health, sex and diet of the patient; the time of administration; the rate of excretion; the drug combination; the severity of the congestive heart failure; and the form of administration. Typically, in vitro dosage-effect results provide useful guidance on the proper doses for patient administration. Studies in animal models are also helpful. The considerations for determining the proper dose levels are well known in the art and within the skills of an ordinary physician.

Any known administration regimen for regulating the timing and sequence of drug delivery may be used and repeated as necessary to effect treatment in the inventive methods. The regimen may include pretreatment and/or co-administration with additional therapeutic agent(s).

The inventive compounds can be administered alone or in combination with one or more additional therapeutic agent(s) for simultaneous, separate, or sequential use. Examples of an additional therapeutic agent include, without limitation, compounds of this invention; steroids (e.g., hydrocortisones such as methylprednisolone); anti-inflammatory or anti-immune drug, such as methotrexate, azathioprine, cyclophosphamide or cyclosporin A; interferon-β; antibodies, such as anti-CD4 antibodies; agents which can reduce the risk of a second ischemic event, such as ticlopidine; chemotherapeutic agents; immunotherapeutic compositions; electromagnetic radiosensitizers; and morphine. The inventive compounds may be co-administered with one or more additional therapeutic agent(s) either (i) together in a single formulation, or (ii) separately in individual formulations designed for optimal release rates of their respective active agent.

Diagnostic Methods and Kit

This invention further provides a method for detecting in vitro or in vivo a disease, disorder or condition where NAALADase levels are altered, comprising:

(i) contacting a sample of bodily tissue or fluid with a compound of formula I, II or III, as defined above, wherein the compound binds to any NAALADase in the sample; and (ii) measuring the amount of any NAALADase bound to the sample, wherein the amount is diagnostic for the disease, disorder or condition.

Examples of a disease, disorder or condition that is detectable by the inventive method include, without limitation, neurological disorder, glutamate abnormality, neuropathy, pain, compulsive disorder, prostate disease, cancer, TGF-β abnormality, Huntington's disease, diabetes, retinal disorder and glaucoma.

Examples of a bodily tissue or fluid that is used in the inventive method include, without limitation, prostate tissue, ejaculate, seminal vesicle fluid, prostatic fluid, urine, blood, saliva, tears, sweat, lymph and sputum.

The inventive compound may be labeled with a marker using techniques known in the art. Useful markers include, without limitation, enzymatic markers and imaging reagents. Examples of imaging reagents include radiolabels, such as $^{131}I$, $^{111}In$, $^{123}I$, $^{99}Tc$, $^{32}P$, $^{125}I$, $^{3}H$ and $^{14}C$; fluorescent labels, such as fluorescein and rhodamine; and chemiluminescers, such as luciferin.

The amount of NAALADase can be measured using any technique known in the art. Examples of such technique include, without limitation, assays (such as immunometric, calorimetric, densitometric, spectrographic and chromatographic assays) and imaging techniques (such as magnetic resonance spectroscopy (MRS), magnetic resonance imaging (MRI), single-photon emission computed tomography (SPECT) and positron emission tomography (PET)).

This invention further provides a diagnostic kit for detecting a disease, disorder or condition where NAALADase levels are altered, comprising a compound of formula I, II or III, as defined above, labeled with a marker. The kit may further comprise one or more buffering agent(s), agent(s) for reducing background interference, control reagent(s) and/or apparatus for detecting the disease, disorder or condition.

This invention further provides a method for detecting a disease, disorder or condition where NAALADase levels are altered in an animal or a mammal, comprising:

(i) labeling a compound of formula I, II or III, as defined above, with an imaging reagent;

(ii) administering to the animal or mammal an effective amount of the labeled compound;

(iii) allowing the labeled compound to localize and bind to NAALADase present in the animal or mammal; and (iv) measuring the amount of NAALADase bound to the labeled compound, wherein the amount is diagnostic for the disease, disorder or condition.

The amount of NAALADase can be measured in vivo using any known imaging technique, as described above.

Incorporation by Reference

The relationship between NAALADase inhibitors and glutamate, and the effectiveness of NAALADase inhibitors in treating and detecting various diseases, disorders and conditions have been discussed in U.S. Pat. Nos. 5,672,592, 5,795,877, 5,804,602, 5,824,662, 5,863,536, 5,977,090, 5,981,209, 6,011,021, 6,017,903, 6,025,344, 6,025,345, 6,046,180, 6,228,888, 6,265,609, 6,372,726, 6,395,718, 6,444,657, 6,452,044, 6,458,775 and 6,586,623; International Publications Nos. WO 01/91738, WO 01/92274 and WO 03/057154; and other references generally known in the art. The present inventors hereby incorporate by reference, as though set forth herein in full, the entire contents of the aforementioned references, particularly their discussions, figures and data regarding the effectiveness of NAALADase inhibitors in inhibiting angiogenesis; in effecting TGF-β activity; in diagnosing a disease, disorder or condition; and in treating glutamate abnormality, compulsive disorder, ischemia, spinal cord injury, demyelinating diseases, Parkinson's disease, ALS, alcohol dependence, nicotine dependence, cocaine dependence, prostate disease, cancer, diabetic neuropathy, pain, schizophrenia, anxiety, anxiety disorder, memory impairment, Huntington's disease, diabetes, retinal disorders and glaucoma. Since the inventive compounds have been found by the present inventors to inhibit NAALADase activity or convert into compounds that inhibit NAALADase activity, they are expected to have the same uses as the NAALADase inhibitors disclosed in the patents and publications incorporated by reference.

Pharmaceutical Compositions

This invention further provides a pharmaceutical composition comprising:

(i) an effective amount of a compound of formula I, II or III; and (ii) a pharmaceutically acceptable carrier.

The inventive pharmaceutical composition may comprise one or more additional pharmaceutically acceptable ingredient(s), including without limitation one or more wetting agent(s), buffering agent(s), suspending agent(s), lubricating agent(s), emulsifier(s), disintegrant(s), absorbent(s), preservative(s), surfactant(s), colorant(s), flavorant(s), sweetener(s) and additional therapeutic agent(s).

The inventive pharmaceutical composition may be formulated into solid or liquid form for the following: (1) oral administration as, for example, a drench (aqueous or nonaqueous solution or suspension), tablet (for example, targeted for buccal, sublingual or systemic absorption), bolus, powder, granule, paste for application to the tongue, hard gelatin capsule, soft gelatin capsule, mouth spray, emulsion and microemulsion; (2) parenteral administration by, for example, subcutaneous, intramuscular, intravenous or epidural injection as, for example, a sterile solution, suspension or sustained-release formulation; (3) topical application as, for example, a cream, ointment, or controlled-release patch or spray applied to the skin; (4) intravaginal or intrarectal administration as, for example, a pessary, cream or foam; (5) sublingual administration; (6) ocular administration; (7) transdermal administration; or (8) nasal administration.

EXAMPLES

Example 1

Preparation of
3-(2-oxo-tetrahydro-thiopyran-3-yl)propionic acid

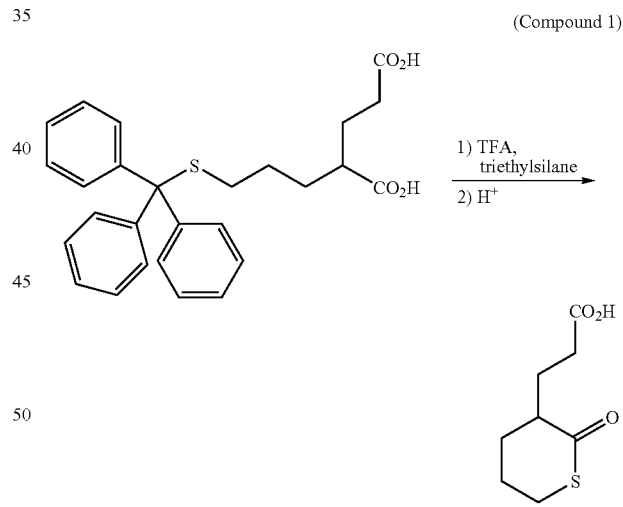

To a solution of 2-[3-(tritylthio)mercaptopropyl]pentanedioic acid (150 g, 0.33 mol) in dichloromethane (500 mL) was added dropwise trifluoroacetic acid (110 mL) over 30 minutes. After being stirred for an additional 30 minutes, a solution of triethylsilane (45 mL, 0.33 mol) in dichloromethane (50 mL) was added and the mixture was stirred at 45° C. for 1 hour. The volatiles were removed in vacuo and the residue was triturated with hexanes (500 mL×2). The oily residue was dissolved in toluene (500 mL) containing 10-camphorsulfonic acid (14 g) and refluxed for 6 hours. The liberated water was removed using a Dean-Stork azeotropic adapter. Toluene was then distilled off and the residue was purified by silica gel chromatography (EtOAc/hexanes, 1/4). Subsequent recrystallization from EtOAc/hexanes afforded 23.3 g of 3-(2-oxotetrahydro-2H-thiopyran-3-yl)propanoic acid as a white solid (37% yield): $^1$H NMR (CD$_3$OD) δ 1.65-1.78 (m, 2H), 2.05-2.18 (m, 4H), 2.35-2.48 (m, 2H), 2.65-2.74 (m, 1H), 3.13-3.29 (m, 2H); $^{13}$C NMR (CD$_3$OD) δ 23.3, 27.4, 29.3, 31.2, 32.3, 50.0, 177.0, 206.4. Analysis calculated for C$_8$H$_{12}$O$_3$S: C, 51.04; H, 6.43; S, 17.03. Found: C, 51.08; H, 6.38; S, 17.16.

Example 2

Preparation of 3-[2-oxotetrahydro-2H-thiopyran-3-yl)methyl]benzoic acid

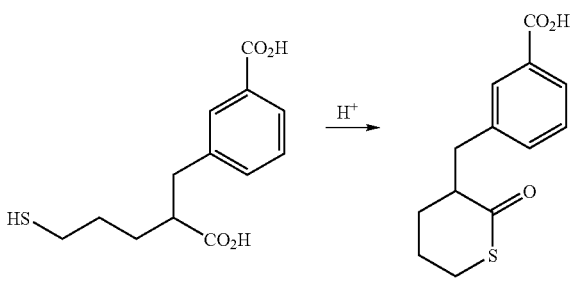

A solution of 3-(2-carboxy-5-mercaptopentyl)benzoic acid (5.12 g, 20 mmol) and 10-camphorsulfonic acid (500 mg) in toluene (30 mL) was refluxed for 6 hours. The liberated water was removed using a Dean-Stork azeotropic adapter. Toluene was then distilled off under reduced pressure and the residue was purified by silica gel chromatography (EtOAc/hexanes, 1:4). Fractions containing the product were collected, evaporated and recrystallized from EtOAc/hexanes to afford 3.2 g of 3-[(2-oxotetrahydro-2H-thiopyran-3-yl)methyl]benzoic acid as a white solid (67% yield): $^1$H NMR (CDCl$_3$) δ 1.58-1.68 (m, 1H), 1.90-2.02 (m, 2H), 2.04-2.13 (m, 1H), 2.68 (m, 1H), 2.78-2.86 (m, 1H), 3.08-3.19 (m, 2H), 3.37-3.44 (m, 1H), 7.38-7.48 (m, 2H), 7.93 (brs, 1H), 7.94-8.02 (m, 1H); $^{13}$C NMR (CDCl$_3$) δ 22.6, 27.8, 31.1, 36.8, 52.0, 128.8, 129.2, 129.8, 131.3, 135.3, 140.1, 172.6, 203.7. Analysis calculated for C$_{13}$H$_{14}$O$_3$S: C, 62.38; H, 5.64; S, 12.81. Found: C, 62.19; H, 5.65; S, 12.59.

Example 3

Preparation of 4-{[(1-oxo-3,4-dihydro-1H-isothiochromen-8-yl)oxy]methyl}benzoic acid

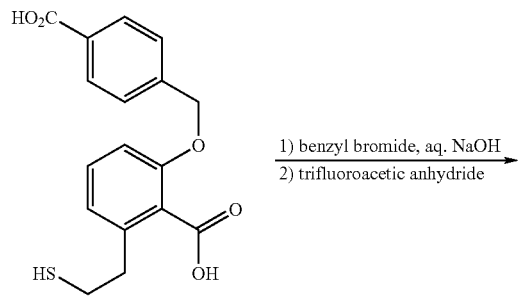

1) benzyl bromide, aq. NaOH
2) trifluoroacetic anhydride

-continued

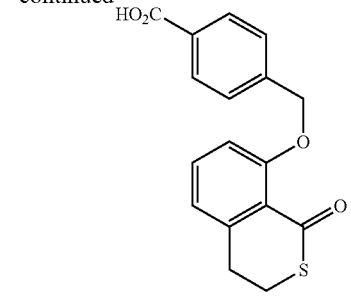

To a solution of 2-[(4-carboxybenzyl)oxy]-6-(2-mercaptoethyl)benzoic acid (1.66 g, 5.0 mmol) in ethanol (80 mL) were added 4% aq. NaOH (20 mL) and a solution of benzylbromide (0.89 g, 5.2 mmol) in ethanol (20 mL) at 0° C. The reaction mixture was stirred at 0° C. for 3 hours. The solvent was removed under reduced pressure and the residue was dissolved in EtOAc. The organic solution was washed with 12 N HCl. The organic layer was dried over MgSO$_4$ and concentrated to give 2.0 g of white solid. This solid was dissolved in trifluoroacetic anhydride (15 mL) and the resulting mixture was stirred at 60° C. for 2 hours. The volatiles were removed in vacuo and the residue was dissolved in saturated aqueous NaHCO$_3$ at 0° C. followed by acidification with 12 N HCl. The resulting precipitate was recovered by filtration and washed thoroughly with water. The recovered solid was purified by silica gel chromatography (EtOAc/hexanes/AcOH, 1/1/0.02) to give 0.8 g of 4-{[(1-oxo-3,4-dihydro-1H-isothiochromen-8-yl)oxy]methyl}benzoic acid as a white powder (54% yield): $^1$H NMR (DMSO-d$_6$) δ 3.15-3.30 (m, 4H), 5.26 (s, 2H), 7.02-7.07 (m, 1H), 7.20-7.27 (m, 1H), 7.53-7.60 (m, 1H), 7.66-7.72 (m, 2H), 8.00-8.05 (m, 2H); $^{13}$C NMR (DMSO-d$_6$) δ 28.7, 31.6, 69.2, 113.2, 121.2, 121.5, 126.6, 123.3, 130.0, 134.0, 142.0, 143.8, 156.2, 167.1, 187.2. Analysis calculated for C$_{13}$H$_{14}$O$_3$S: C, 62.38; H, 5.64; S, 12.81. Found: C, 62.19; H, 5.65; S, 12.59.

Example 4

Preparation of 3-(1-oxo-3,4-dihydro-1H-isothiochromen-8-yl)benzoic acid

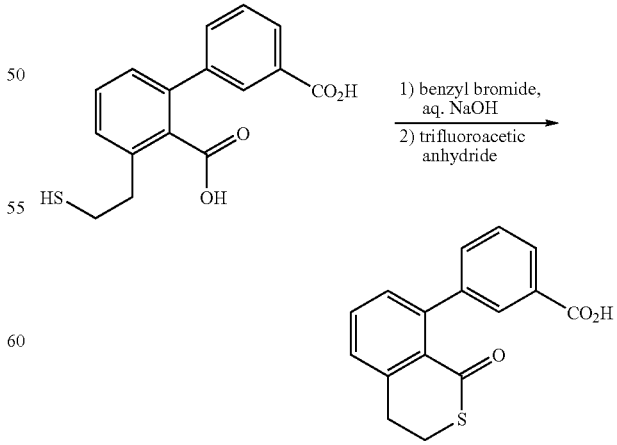

1) benzyl bromide, aq. NaOH
2) trifluoroacetic anhydride

By the method previously outlined in Example 3 but using 3-(2-mercaptoethyl)-[1,1'-biphenyl]-2,3'-dicarboxylic acid was made 3-(1-oxo-3,4-dihydro-1H-isothiochromen-8-yl)benzoic acid (34% yield): $^1$H NMR (DMSO-d$_6$) δ 3.21-3.42 (m, 4H), 7.27-7.37 (m, 1H), 7.45-7.53 (m, 3H), 7.57-7.64 (m, 1H), 7.75-7.79 (m, 1H), 7.87-7.94 (m, 1H).

Example 5

Efficacy of NAALADase Inhibitors in Treating Retinal Disorders

Four groups of rats received daily insulin injections to maintain their glucose levels at about 350 mg/dl. Starting at the onset of hyperglycemia, NAALADase inhibitor 2-(3-sulfanylpropyl)-pentanedioic acid (Compound B) was administered daily for 6 months to one group of BB/W rats at a dose of 10 mg/kg and to a second group of BB/W rats at a dose of 30 mg/kg. A third group of BB/W rats and a fourth group of non-diabetic rats received daily vehicle treatment (50 mM Hepes buffered saline).

After 6 months of treatment with Compound B or vehicle treatment, the rats were sacrificed and their eyes were removed. From each rat, one eye was processed for elastase digest while the other eye was processed for transmission electron microscopy (TEM) and basement membrane (BM) thickness.

Elastase Digests

Retinal digests were prepared using elastase on retinas as described in Layer, N., *Invest Opthalmol V is Sci* (1993) 34:2097. Eyes were removed from recently killed BB/W rats (n=30) and age-matched transgenic controls (n=12). The retinas (n=12) were fixed at room temperature by immersing the whole eye (slit at limbus) in 4% (w/v) paraformaldehyde in 50 mmol/L Na—K phosphate buffer with 8% sucrose. The fixed retinas were rinsed in deionized water and were incubated for 3 minutes in a 37° C. agitating water bath in 40 units/mL elastase in Na—K phosphate buffer with 150 mmol/L NaCl and 5 mmol/L ethylenediamine tetraacetic acid (EDTA), pH 6.5. The tissues were washed overnight in 100 mmol/L Tris-HCL (pH 8.5) and then transferred to deionized water for removal of the loosened vitreous and digested neural elements by gentle agitation using the sides of closed forceps and the sides and ends of very fine brushes. After all loose tissues were removed, the retinas were incubated once more in fresh enzyme for 3 minutes and then subjected to a second overnight wash at room temperature in Tris-HCl buffer. On the third day, the retinas were again transferred to deionized water for additional removal of digested neural elements. The vascular network that was completely free of nonvascular elements was mounted flat by flotation in Ca$^{2+}$ and Mg$^{2+}$ free Dulbecco's Phosphate-Buffered Saline (PBS) on siliconized slides (#S1308, Oncor, Gaithersburg, Md.). After air drying in a dust free environment, the mounts of the retinal microvasculature were stained using periodic acid Schiff reaction and hematoxylin counterstaining, as described in Luna, L., ed. *Manual of Histologic Staining Methods of the Armed Forces Institute of Pathology* (1968) McGraw-Hill, New York, N.Y. The preparations were then examined by light microscopy and photographed.

Endothelial/Pericyte (E/P) Ratios

The stained and intact retinal whole mounts were coded and counted, as described in Cuthbertson, R., *Invest Opthalmol V is Sci*. (1986) 27:1659-1664).

Ten fields at ×100 magnification were counted for endothelial and pericyte cells using previously described morphologic criteria (see Kuwabara, T., *Arch Opthalmol*. (1960) 64:904-911). In every sample, at least 200 cells were counted from the mid zone of the retina. Mean values for endothelial cell/pericyte (E/P) ratios were initially calculated in 3 retinas from each of the 4 groups of rats.

Evaluation of BM Thickness

Each eye was fixed in 4% glutaraldehyde and dissected free of sclera and choroids, then trimmed and postfixed in 1% osmium tetroxide. After dehydration and embedding, thin sections were stained with uranyl acetate and lead citrate. Initially, BM thickness of retinal capillaries from 3 non-diabetic rats receiving vehicle, 3 diabetic animals receiving 10 mg/kg Compound B, and 3 diabetic rats receiving 30 mg/kg Compound B were compared with 3 diabetic rats receiving a vehicle. At least 10 capillaries per eye from the inner nuclear and plexiform layers were photographed at a magnification of 10,000×. Exact magnification was determined for each set of negatives with a 28,800 line/inch calibration grid. Negatives were enlarged 3×. Measurements, to the nearest 0.25 mm, were made of the BM surrounding the endothelial cell and were taken perpendicular to the plane of the BM, as described in Bendayan, M., *J. Electron Microsc Techn* (1984) 1:243-270; and Gunderson, *J. Microscopy* (1980) 121:65-73). At least 20 measurements were taken for each capillary and the BM thickness was expressed as an average of 20 measurements.

Statistical Analysis

Statistical analysis for comparison among groups was performed using one way analysis of variance (ANOVA) and Student's t test. Significance was defined as a value of $p<0.05$. Values were reported as mean±standard errors from the mean (SEM), unless otherwise noted.

Results of Elastase Digest Preparations and E/P Ratios

Figure 2:
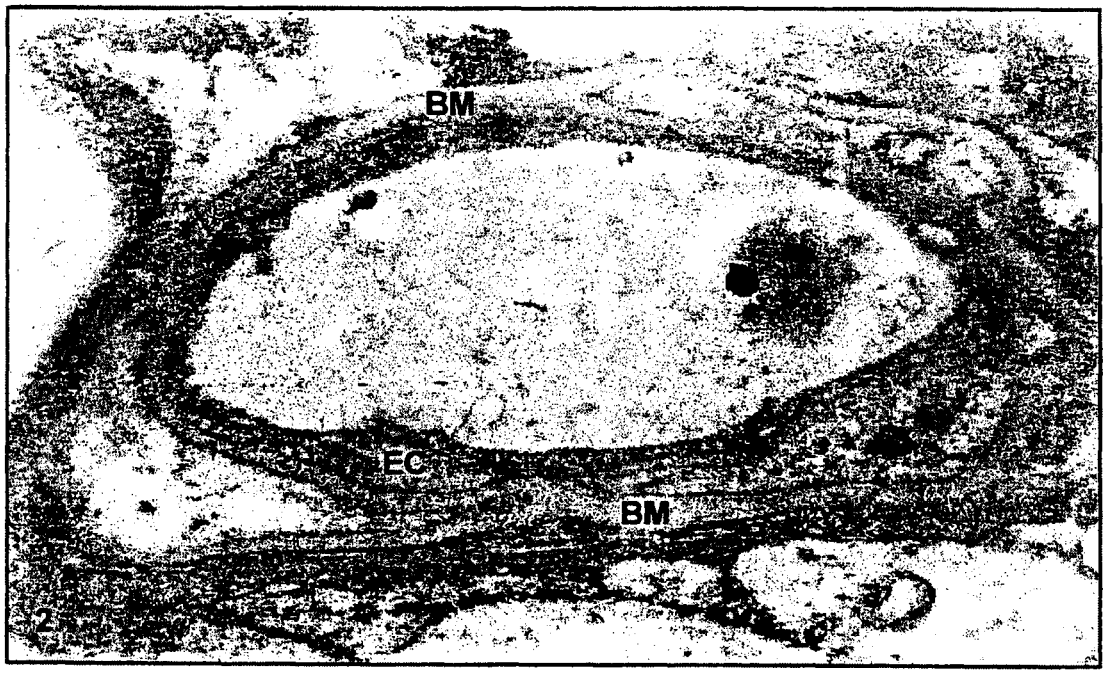
FIG. 2 is a 27,000× magnified photograph of a retinal blood vessel from a diabetic rat after six months of treatment with a vehicle.
Figure 3:
FIG. 3 is a 27,000× magnified photograph of a retinal blood vessel from a diabetic rat after six months of treatment with Compound B.

In intact whole mounts of retinal digests the endothelial cell nuclei, seen medially within the vessel wall, were large, oval, pale staining and protruded lumenally. Pericyte nuclei, seen more laterally, were dark staining, small, round and protruded prominently away from the vessel wall. E/P counts were taken from mid zones of the retinas. The attached figures show 27,000× magnified photographs of retinal blood vessels from a control, non-diabetic rat (FIG. 1), from a control, diabetic rat after 6 months of treatment with a vehicle (FIG. 2), and from a diabetic rat after 6 months of treatment with Compound B (FIG. 3).

NAALADase inhibition had no effect on blood glucose or body weight. The high dose (30 mg/kg) treatment with Compound B resulted in a 29.0% reduction in BM thickness (diabetic vehicle=101.0±14.81 nm and diabetic NAALADase$_{30}$=71.7±4.07 nm), while the low dose (10 mg/kg) treatment with Compound B resulted in an 18.5% decrease in BM thickness (NAALADase$_{10}$=82.3±4.07 nm). The high dose treatment with Compound B also resulted in a 33.0% reduction of endothelial cell to pericyte ratios (diabetic vehicle=3.0±0.1 and NAALADase$_{30}$=2.0±0.9), while the low dose treatment with Compound B resulted in a 16.7% reduction of the same cell ratios (NAALADase$_{10}$=2.5±0.5). See TABLE II.

TABLE II

| RAT GROUP | BM THICKNESS (nm) ± SD | E/P RATIO |
|---|---|---|
| NON-DIABETIC CONTROLS | 56.3 ± 4.78 | 1.8 ± 0.07 |
| DIABETIC VEHICLE | 101 ± 14.81 | 3.0 ± 0.1 |
| DIABETIC 30 MG/KG NAAALADASE INHIBITOR | 71.7 ± 4.07 | 2.0 ± 0.4 |
| DIABETIC 10 MG/KG NAALADASE INHIBITOR | 82.3 ± 4.07 | 2.5 ± 0.5 |

Conclusions

While the BB/W rats demonstrated an early change typically associated with diabetic retinopathy (pericyte loss and BM thickening), they did not show significant numbers of microanuerysms also typical of diabetic retinopathy or areas of acellular capillaries usually seen in a more advanced disease. The retinopathy observed in BB/W rats has been previously characterized in Chakrabarti, *Diabetes* (1989) 38:1181-1186.

The results show that treatment with a NAALADase inhibitor causes improvement in retinal pathology of diabetic rats. Specifically, the NAALADase inhibitor prevented pericyte loss and BM thickening in retinal vessels.

Example 6

Protective Effect of NAALADase Inhibitors in Experimental Rat Glaucoma

Experimental Protocol

All experiments complied with the Association for Research in Vision and Opthalmology Statement for the Use of Animals in Ophthalmic and Vision Research. 82 male Brown Norway rats (*Rattus norvegicus*), each weighing approximately 250 gm, were treated using procedures approved by the Animal Care Committee of the Johns Hopkins University School of Medicine. The rats were housed with a 12 hour light/12 hour dark cycle and fed ad libitum.

Experimental Glaucoma

Unilateral elevation of intraocular pressure ("IOP") was produced in 56 rats by microinjection of hypertonic saline into episcleral veins, following procedures described in Morrison, J. et al., *IOVS* (March 1998) 39:526-531. Beginning on the day of IOP elevation, the rats were treated daily with intraperitoneal injections of either a vehicle (23 rats with 50 mM HEPES-buffered saline) or a NAALADase inhibitor (11 rats with 10 mg/kg of Compound A and 22 rats with 10 mg/kg of Compound B). 11 saline treated rats, 11 Compound A treated rats and 11 Compound B treated rats were sacrificed at 8 weeks, and the remaining rats at 12 weeks, after initial IOP elevation.

Optic Nerve Transection

The optic nerve was transected unilaterally in 26 rats under intraperitoneal pentobarbital anesthesia. The conjunctiva was opened with scissors and the optic nerve was exposed by traction on extraocular muscles. The transection was performed with microscissors 5 mm posterior to the globe, with specific attention to avoidance of injury to major ocular blood vessels. Immediately after transection, the retina was examined opthalmoscopically to assure that the retinal arterial blood supply was not disrupted. The conjunctiva was closed with absorbable suture and the eye dressed with antibiotic ointment. Beginning on the day of transection, the rats were treated daily with intraperitoneal injections of either a vehicle (9 rats with 50 mM HEPES-buffered saline) or a NAALADase inhibitor (8 rats with 10 mg/kg of Compound A and 9 rats with 10 mg/kg of Compound B). 5 saline treated rats, 3 Compound A treated rats and 4 Compound B treated rats were sacrificed at 2 weeks, and the remaining rats at 4 weeks, after transection.

Optic Nerve Counting

The rats were sacrificed by exsanguination under deep pentobarbital anesthesia. They were perfused through the heart with 2% paraformaldehyde/2% glutaraldehyde in 0.1 M phosphate buffer, pH 7.2, and the eyes with attached optic nerves were removed. Cross-sections of the optic nerves from both experimental (glaucoma or transection) and control eyes was removed 1.5 mm posterior to the globe, 1 mm in thickness, and post-fixed in 2% osmium tetroxide in buffer. These were processed into epoxy resin, sectioned at 1 micron and stained with toluidine blue.

The area of each optic nerve cross-section was measured by outlining its outer border at 10× magnification on an image analysis system (Universal Imaging Corp., Westchester, Pa.) with Synsys digital camera and Metamorph software. Three area measurements were taken and the mean value was determined. To measure the density and fiber diameter distributions, images were captured with a 100× phase contrast objective from 10 different areas of each nerve. These were edited to eliminate non-neural objects and the size of each axon internal to the myelin sheath (its minimum diameter) and the density of axons/square mm were calculated for each image and nerve. The mean density was multiplied by total nerve area to yield fiber number for each nerve. The total fiber number in glaucoma or transection nerves was compared to the normal, fellow eye of each rat to yield a percent loss value. The number of axons counted among the 10 images was approximately 20% of the 80-90,000 axons in normal rat nerves. The person measuring the number of axons was masked to the protocol conducted on the nerves.

Results

Experimental Glaucoma

The mean fiber percent difference in the saline-treated, control rats was significantly lower in their glaucoma eyes compared to their normal eyes, with a mean fiber loss of 14.44±5.75% (n=11 rats; TABLE III) in the 8 week follow-up group, and 8.15±7.84% in the 12 week follow-up group (n=12 rats; TABLE IV).

By contrast, there was no significant loss of fibers in either the 8 week or 12 week NAALADase inhibitor-treated rats. The mean percent fiber loss in each NAALADase inhibitor-treated group was statistically less than the loss in the saline-treated, control groups (at 8 weeks, p=0.05 for Compound A and p=0.02 for Compound B).

TABLE III

EXPERIMENTAL GLAUCOMA RESULTS

| 8 Week Group | N | IOP Integral Difference | FIBER NUMBER | Percent Difference |
|---|---|---|---|---|
| Compound A | 11 | 85 ± 37.5 | 79156 ± 2436* | -1.82 ± 2.92 |
| Compound B | 11 | 116 ± 33.2 | 80785 ± 2121** | -0.82 ± 2.97 |
| Control | 11 | 104 ± 26.4 | 68295 ± 4617 | 14.44 ± 5.75 |

TABLE IV

EXPERIMENTAL GLAUCOMA RESULTS

| 12 Week Group | N | IOP Integral Difference | FIBER NUMBER | Percent Difference |
|---|---|---|---|---|
| Compound B | 11 | 109 ± 45.2 | 90504 ± 1718 | -3.21 ± 2.86 |
| Control | 12 | 158 ± 66.5 | 79827 ± 6783 | 8.15 ± 7.84 |

IOP Integral Difference = difference in IOP exposure between glaucoma eye and normal eye in each rat (mm Hg - days).
Percent Difference = mean percent difference in fiber number between glaucoma and normal eye in each rat (positive value indicates fewer fibers in the glaucoma eye).
The differences in IOP Integral Difference are not significant (p > 0.05). The differences in Percent Difference between drug-treated and saline-treated, control rats at 8 weeks post insult are significant (p = 0.05* and p = 0.02**).

Optic Nerve Transection

The experimental transection data suggest a slowing or rescue of ultimate retinal ganglion cell (RGC) death in rats treated with NAALADase inhibitors at 2 weeks after transection. At 2 weeks after transection, both drug-treated groups had more remaining RGC axons than did the saline-treated, control group, judged either by absolute number of fibers or percent difference between transected eye and normal eye in each rat (TABLE V). Rats treated with Compound A and Compound B had, respectively, three times and twice as many remaining axons as the saline-treated rats. All or nearly all RGC die within the first 2 months after transection, regardless of any pharmacological treatment. Thus, by 4 weeks after transection, more than 80% of RGC axons were gone in all groups (TABLE VI). At 4 weeks after transection, there were no significant differences between the drug-treated rats and the saline-treated rats.

TABLE V

OPTIC NERVE TRANSECTION

| 2 Weeks Survival | N | Fiber Number | Percent Difference |
|---|---|---|---|
| Compound A | 3 | 26,426 ± 23,025 | 65.3 ± 30.9 |
| Compound B | 4 | 19,550 ± 11,383 | 75.3 ± 14.8 |
| Control | 5 | 8,220 ± 9,337 | 90.2 ± 10.7 |

TABLE VI

OPTIC NERVE TRANSECTION

| 4 Weeks Survival | N | Fiber Number | PERCENT DIFFERENCE |
|---|---|---|---|
| Compound A | 5 | 13,599 ± 7,868 | 82.4 ± 8.9 |
| Compound B | 5 | 5,162 ± 5,017 | 93.4 ± 6.2 |
| Control | 4 | 10,449 ± 8,157 | 86.9 ± 10.6 |

Percent Difference = mean percent difference in fiber number between glaucoma and normal eye in each rat (positive value indicates fewer fibers in the glaucoma eye).
The differences in Percent Difference between drug-treated and saline-treated, control rats are not statistically significant ($p = 0.05$).

Example 7

Effects of NAALADase Inhibitor on Development of Morphine Tolerance

Experimental Protocol

Subjects

Male C57/BL mice (IMP, Lodz, Poland), 22-24 g of body weight were group-housed in the standard laboratory cages and kept in a temperature-controlled colony room ($21 \pm 2°$ C.) with a 12-hour light/dark cycle (light on: 07:00, off: 19:00). Commercial food and tap water were available ad libitum. Each experimental group consisted of 7-28 mice per treatment. All mice were used only once.

Apparatus for Experiments 1-2

A standardized tail-flick analgesia meter (Columbus, Ohio, USA, model 33), adjusted to sensitivity of "10" with radiant heat source and connected to an automatic timer was used to assess antinociceptive responses. The intensity of the heat stimulus was adjusted so that the baseline tail-flick latency was ~3 seconds. A maximum latency of 10 seconds (i.e., cut-off) was used to minimize damage to the tail. The tail withdrawal latency was measured from the start of heat stimulus until the mouse exhibited a flick of the tail. Each response assessment consisted of two separate measurements taken at different portions of the tail (spaced by 1.5-2 cm) and separated by 15 seconds. The mean of these responses was used for subsequent comparisons.

Morphine antinociceptive potency was investigated with the use of cumulative dose-response curves that allowed for minimization of the animal number used (Paronis and Holtzman 1991). After adaptation and baseline trials, each mouse was injected s.c. with a low dose of morphine (1 mg/kg). Thirty min later, the mouse was retested and injected with the next dose of morphine that was increased by quarter of a log unit. Thus, because the initial dose of morphine was 1.0 mg/kg, the next dose was 1.78 mg/kg, for a cumulative dose of 2.8 mg/kg. This procedure continued until either the mouse did not move his tail within the cut-off time or until there was a plateauing of the dose-response curve, so that the latency did not increase from one dose to the next. Each analgesic responder was not subjected to further tail flick assessments but was injected with the subsequent dose of morphine so that every animal received the same total dose of morphine during a given test.

Effects on Morphine Tolerance (Experiment 1) and Acute Effects in the Tail-Flick Test (Experiment 2)

Experiment 1 was carried out to investigate the effect of 2-PMPA on the development of morphine tolerance. On day 1 (test # 1), the first measurement of morphine antinociceptive potency was performed, followed by 6 days of bid morphine injections (10 mg/kg, s.c., 7:30 and 17:30) (Elliott et al. 1994; Popik et al. 2000b). Pretreatment with 2-(phosphonomethyl) pentanedioic acid (2-PMPA; 30, 50 or 100 mg/kg, i.p.) or memantine (7.5 mg/kg, s.c., a "positive control") was given at 30 minutes prior to each morphine dose on days 2-7. On day 8 (test #2), the second measurement of morphine antinociceptive potency was carried out. The degree of morphine tolerance was assessed by comparing the morphine antinociceptive potencies (cumulative dose-response curves) obtained in tests #1 and #2.

Experiment 2 was designed to determine whether 2-PMPA might itself produce antinociceptive effects and/or affect the antinociceptive effects of morphine. Morphine (1.5 or 3 mg/kg, s.c.) was administered 30 min after injection of 100 mg/kg of 2-PMPA or placebo, administered i.p. The 3 mg/kg dose of morphine corresponds to the antinociceptive $ED_{50}$ dose in these test conditions (data not shown).

Results

Effects of NAALADase Inhibitor on Development of Morphine Tolerance (Experiment 1)

There were no differences in antinociceptive morphine $ED_{50}$ values on test #1 among groups (TABLE VII). Treatment with 10 mg/kg bid of morphine produced 6.44 fold increase in the $ED_{50}$ values as determined on test #2. In contrast, pretreatment with memantine, 50 or 100 (but not 30) mg/kg of 2-PMPA given prior to each dose of morphine attenuated the development of morphine tolerance. The effects of 2-PMPA were related to the dose. This was evidenced by a significant decrease in both test #2 $ED_{50}$ values (statistically significant for the dose 100 mg/kg) and antinociceptive morphine fold shifts of 2-PMPA for the doses of 100 and 50 mg/kg, as compared with the control group that received placebo+morphine (Table VII). Similarly, memantine (7.5 mg/kg) produced an inhibition of morphine tolerance.

TABLE VII

EFFECTS OF 2-PMPA AND MEMANTINE ON THE DEVELOPMENT OF TOLERANCE TO MORPHINE

| Treatment/dose mg/kg (N) | Test #1 $ED_{50}$ | Test #2 $ED_{50}$ | Fold Shift |
|---|---|---|---|
| Placebo + Morphine (8) | 1.49 ± 0.26 | 8.85 ± 2.22 | 6.44 ± 1.17 |
| Placebo + Placebo (8) | 2.23 ± 0.42 | 3.28 ± 0.47* | 1.70 ± 0.29* |
| 2-PMPA 30 + Morphine (9) | 2.00 ± 0.43 | 9.47 ± 2.13 | 5.20 ± 1.26 |
| 2-PMPA 50 + Morphine (9) | 1.87 ± 0.34 | 5.41 ± 1.11 | 3.20 ± 0.66* |
| 2-PMPA 100 + Morphine (10) | 1.59 ± 0.30 | 3.49 ± 0.83* | 2.70 ± 0.57* |
| Memantine 7.5 + Morphine (8) | 1.51 ± 0.29 | 3.52 ± 0.88* | 2.60 ± 0.49* |
| ANOVA: F(5, 46) = | 0.71; ns | 3.891; P < 0.01 | 4.555; P < 0.01 |

Effects of 2-PMPA on the Tail-flick Response and Antinociceptive Effects of Morphine (Experiment 2)

Analysis of areas under curve (AUC) revealed that treatment with placebo+1.5 and 3 mg/kg of morphine produced statistically significantly longer tail-flick responses compared to placebo+placebo treatment. In contrast, 100 mg/kg of 2-PMPA+placebo treatment did not affect tail-flick responses as compared to placebo+placebo treatment. Moreover, this dose of 2-PMPA did not affect antinociceptive effects of 1.5 or 3 mg/kg of morphine (FIG. 4).

Figure 4:
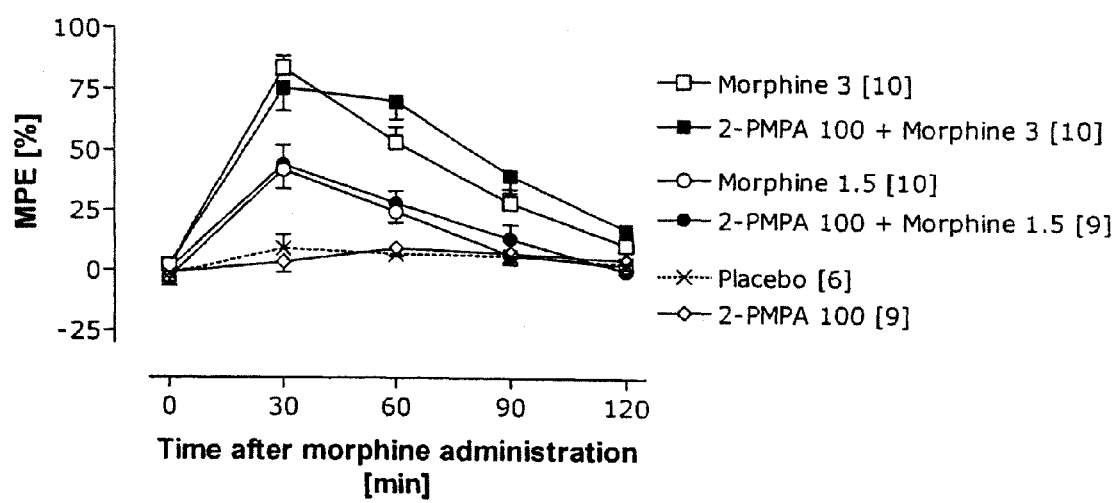
FIG. 4 is a graph plotting the time courses of tail-flick responses of mice treated with a placebo, a NAALADase inhibitor, morphine, or a NAALADase inhibitor with morphine.
Figure 5:
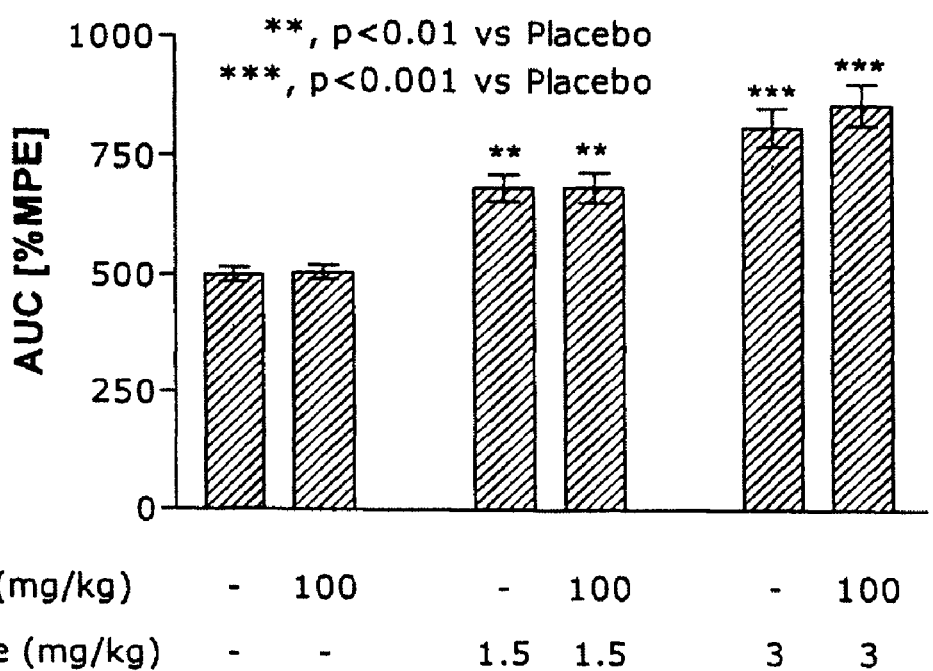
FIG. 5 is a bar graph plotting the mean±S.E.M. Area Under Curve (AUC) values.

Presented in FIG. 4 are the time courses of tail-flick responses of mice treated with combination of 2-PMPA and morphine. The N is given in brackets. Presented in FIG. 5 are mean±S.E.M. Area Under Curve (AUC) values calculated on the same data. One way ANOVA F(5.48)=19.28, P<0.0001 and post-hoc Newman-Keul's test revealed that the treatment with placebo+morphine 1.5 mg/kg and with 100 mg/kg 2-PMPA+morphine 1.5 mg/kg differed significantly (, P<0.01) from placebo+placebo treatment. Similarly, treatment with placebo+morphine 3 mg/kg and that with 100 mg/kg 2-PMPA+morphine 3 mg/kg differed significantly (*, P<0.001) from placebo+placebo treatment. Effects of 100 mg/kg of 2-PMPA+placebo treatment did not differ from placebo+placebo treatment. Effects of placebo+respective doses of morphine did not differ from the effects of 2-PMPA+respective doses of morphine.

Example 8

A patient is suffering from any disease, disorder or condition where NAALADase levels are altered, including any of the diseases, disorders or conditions described above. The patient may then be administered an effective amount of an inventive compound. It is expected that after such treatment, the patient would not suffer any significant injury due to, would be protected from further injury due to, or would recover from the disease, disorder or condition.

All publications, patents and patent applications identified above are herein incorporated by reference.

The invention being thus described, it will be apparent to those skilled in the art that the same may be varied in many ways without departing from the spirit and scope of the invention. Such variations are included within the scope of the invention to be claimed.

We claim:

1. A compound of formula II:

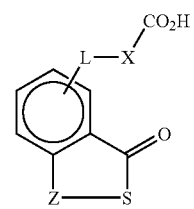

or a pharmaceutically acceptable salt, an optical isomer or a mixture of optical isomers of the compound, wherein:
X is $C_1$-$C_4$ alkylene, $C_2$-$C_4$ alkenylene, $C_2$-$C_4$ alkynylene, $C_3$-$C_8$ cycloalkylene, $C_5$-$C_7$ cycloalkenylene or Ar, wherein the alkylene, alkenylene, alkynylene, cycloalkylene or cycloalkenylene is unsubstituted or substituted with one or more substituents(s);
L is a bond, —$CR^1R^2$—, —O—, —S—, —$SO_2$— or —$NR^1$—;
Z is —$(CR^5R^6)_n$—;
n is 1, 2, 3 or 4;
Ar is a bivalent aryl or heteroaryl radical that is unsubstituted or substituted with one or more substituents(s); and
$R^1$, $R^2$, $R^5$ and $R^6$ are independently hydrogen, $C_1$-$C_4$ alkyl or $C_2$-$C_4$ alkenyl, wherein the alkyl or alkenyl is unsubstituted or substituted with one or more substituent(s).

2. The compound of claim 1, wherein:
X is a $C_1$-$C_4$ alkylene or Ar, wherein said alkylene and Ar are unsubstituted or substituted with one or more substituent(s); and
Ar is phenylene, biphenylene or benzylene, wherein said phenylene, biphenylene and benzylene are unsubstituted or substituted with one or more substituents independently selected from carboxy, halo, nitro, $C_1$-$C_4$ alkyl, $C_1$-$C_4$ alkoxy, phenoxy, or benzyloxy.

3. The compound of claim 2, wherein:
L is a bond; and
X is phenylene.

4. The compound of claim 3, wherein:
n is 2.

5. The compound of claim 4, wherein:
$R^5$ and $R^6$ are both hydrogen.

6. The compound of claim 1, wherein the compound is 3-(1-oxo-isothiochroman-8-yl)-benzoic acid.

7. The compound of claim 2, wherein:
L is O; and
X is benzylene or $C_1$-$C_4$ alkylene, wherein said alkylene is substituted with phenylene.

8. The compound of claim 7, wherein:
n is 2.

9. The compound of claim 8, wherein:
$R^5$ and $R^6$ are both hydrogen.

10. The compound of claim 1, wherein the compound is 3-(1-oxo-isothiochroman-8-yloxymethyl)-benzoic acid.

11. A pharmaceutical composition comprising:
an effective amount of a compound of claim 1; and
a pharmaceutically acceptable carrier.

12. The pharmaceutical composition of claim 11, wherein the compound is 3-(1-oxo-isothiochroman-8-yl)-benzoic acid.

13. The pharmaceutical composition of claim 11, wherein the compound is 3-(1-oxo-isothiochroman-8-yloxymethyl)-benzoic acid.

* * * * *